United States Patent
Jones et al.

(10) Patent No.: US 10,890,587 B2
(45) Date of Patent: Jan. 12, 2021

(54) METHOD AND COMPOSITIONS FOR DETECTING AN ADENOMA-ADENOCARCINOMA TRANSITION IN CANCER

(71) Applicant: Quest Diagnostics Investments Incorporated, Wilmington, DE (US)

(72) Inventors: Daniel Jones, San Juan Capistrano, CA (US); Kevin J. Arvai, San Juan Capistrano, CA (US); Ya-Hsuan Hsu, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 195 days.

(21) Appl. No.: 15/113,891

(22) PCT Filed: Jan. 27, 2015

(86) PCT No.: PCT/US2015/013061
§ 371 (c)(1),
(2) Date: Jul. 25, 2016

(87) PCT Pub. No.: WO2015/116578
PCT Pub. Date: Aug. 6, 2015

(65) Prior Publication Data
US 2016/0341730 A1 Nov. 24, 2016

Related U.S. Application Data

(60) Provisional application No. 61/932,543, filed on Jan. 28, 2014.

(51) Int. Cl.
*G01N 33/574* (2006.01)
*C12Q 1/6886* (2018.01)

(52) U.S. Cl.
CPC ..... *G01N 33/57419* (2013.01); *C12Q 1/6886* (2013.01); *C12Q 2600/106* (2013.01); *C12Q 2600/118* (2013.01); *C12Q 2600/156* (2013.01); *C12Q 2600/158* (2013.01); *G01N 2333/47* (2013.01); *G01N 2333/916* (2013.01); *G01N 2800/52* (2013.01); *G01N 2800/56* (2013.01)

(58) Field of Classification Search
CPC ......... G01N 33/57419; G01N 2333/47; G01N 2333/916; G01N 33/5073; C12Q 1/6886; C07K 16/18; C07K 16/30; C12N 5/0695
See application file for complete search history.

(56) References Cited

U.S. PATENT DOCUMENTS

| 6,649,359 B2 | 11/2003 | Mutter et al. |
| 2005/0271638 A1 | 12/2005 | Li et al. |
| 2008/0248026 A1 | 10/2008 | He et al. |
| 2011/0265197 A1* | 10/2011 | Depinho ................. C12N 9/16 800/14 |
| 2011/0287034 A1 | 11/2011 | Frank et al. |
| 2014/0011767 A1* | 1/2014 | Yang .................... C12Q 1/6886 514/64 |
| 2014/0137274 A1 | 5/2014 | Ishikawa |
| 2014/0206543 A1* | 7/2014 | Rogan .................. C12Q 1/6886 506/2 |

FOREIGN PATENT DOCUMENTS

| CN | 1970789 A | 5/2007 |
| WO | WO 2013/081188 A1 | 6/2013 |

OTHER PUBLICATIONS

Chang et al (Pathology Oncology Research, 2007, vol. 13, pp. 326-335) (Year: 2007).*
Agoston et al, Diagnostic Pathology, 2016, vol. 11:61, pp. 1-12 (Year: 2016).*
Frattini et al (British Journal of Cancer, 2007, vol. 97, pp. 1139-1145) (Year: 2007).*
Salovaara et al (Gut, 2002, vol. 51, pp. 56-59) (Year: 2002).*
Abstract of Xia et al (Wuhan Daxue Xuebao, 2003, vol. 23, pp. 24-26) (Year: 2003).*
Abstract of Wu et al (Zhongliu Fangzhi Zazhi, 2004, vol. 11, pp. 237-238) (Year: 2004).*
Abstract of Zhao et al, (Lanzhou Daxue Xuebao, 2008, vol. 34, pp. 4-7) (Year: 2008).*
Ni and Xu (Journal of Zhengzhou University, 2007, vol. 42, pp. 898-900) (Year: 2007).*
Chen et al (World Journal of Gastroenterology, 2007, vol. 13, pp. 699-708) (Year: 2007).*
Ghita et al (Rom J Morphol Embryol, 2012, vol. 53, pp. 549-556) (Year: 2012).*
Pannequin et al (Gastroenterology, 2007, vol. 133, pp. 1554-1568) (Year: 2007).*
Lombardo et al (Gastroenterology, 2011, vol. 140, pp. 297-309) (Year: 2011).*
The abstract of Lu (Zonghua yi xue za zhi, 2008, vol. 88, pp. 610-614) (Year: 2008).*
Roth et al (JNCI, 2012, Vo. 104, pp. 1635-1646) (Year: 2012).*
Office Action and Search Report dated Aug. 28, 2017, in CN Application No. 201580016300.1, with English translation.
Supplementary European Search Report dated Jul. 21, 2017, in EP 15744061.1.

(Continued)

*Primary Examiner* — Karen A. Canella
(74) *Attorney, Agent, or Firm* — Foley & Lardner LLP

(57) ABSTRACT

Methods and kits for detecting alternating spatial expression of PTEN and, optionally, SMAD4, CD44, and/or TP53 in colonic tumors are described. The methods and kits are useful for identifying a cancer stem cell (CSC)-like zone within a colonic tumor, identifying an adenoma-adenocarcinoma (Ad-ACA) transition zone in a colorectal cancer (CRC) tumor, identifying a CRC tumor that contains high-grade adenoma and/or early adenocarcinoma regions, identifying CSCs in a CRC tumor, diagnosing a subject with high-grade colon adenoma and/or early adenocarcinoma, and determining the likelihood that a colonic tumor in a subject will undergo invasive transformation if left untreated.

14 Claims, 5 Drawing Sheets

(56) References Cited

OTHER PUBLICATIONS

Atreya et al., "PTEN expression is consistent in colorectal cancer primaries and metastases and associates with patient survival," Cancer Medicine, Jun. 10, 2013, 2(4):496-506.
Hill et al,. "PTEN, Stem Cells, and Cancer Stem Cells," Journal of Biological Chemistry, May 1, 2009, 284(18):11755-11759.
Khalek et al., "Colon Cancer Stem Cells," Gastrointestinal Cancer Research, Nov. 1, 2010, Suppl:S16-S23.
Penninger et al., "PTEN-Coupling Tumor Suppression to Stem Cells," Science, Dec. 7, 2001, 294:2116-2118.
Roy et al., "Difluorinated-Curcumin (CDF) Restores PTEN Expression in Colon Cancer Cells by Down-Regulating miR-21," PLOS One, Jul. 24, 2013, 8(7):e68546, 1-6.
He et al., "PTEN-Deficient Intestinal Stem Cells Initiate Intestinal Polyposis," Nature Genetics, vol. 39, No. 2, pp. 189-198, Jan. 2007.
International Search Report dated Jun. 26, 2015 in application No. PCT/2015/013061.
Office Action dated Jun. 27, 2018, in CN 201580016300.1, with English translation.
Lin et al., "Expression and significance of Ki-67 and p53 in gallbladder carcinoma tissues," Shangdong Pharmaceutical, Feb. 13, 2009, 49(6):67-68.
Liu et al., "Expression of enhancer of EZH2 and PTEN in benign and malignant gallbladder tissues," Central South University Journal, Jul. 31, 2008, 33(7):618-622, with English abstract on first page.
Liu et al., "Expression of NF-KB/P65 in benign and malignant gallbladder lesions and its clinicopathological significance," Chinese Journal of Clinical Oncology and Rehabilitation, Oct. 31, 2008, 15(5):419-422, with English abstract on first page.
Liu et al., "Identification of musashi-1 and ALDH1 as carcinogenesis, progression, and poor-prognosis related biomarkers for gallbladder adenocarcinoma," Cancer Biomarkers, Dec. 12, 2011, 8(3):113-121.
Yong et al., "Expression and significance of survivin and c-myc in gallbladder carcinoma tissues," Chinese Journal of Coal Industry Medicine, Aug. 31, 2007, 10(8):888-889, with English abstract on first page.
Office Action in BR 112016017132.2 dated Sep. 30, 2019.
Frattini et al., "PTEN loss of expression predicts cetuximab efficacy in metastatic colorectal cancer patients," British Journal of Cancer, 2007, 97(8):1139-1145.
Salovaara et al., "Frequent loss of SMAD4/DPC4 protein in colorectal cancers," Gut, 2002, 51(1):56-59.

* cited by examiner

METHOD AND COMPOSITIONS FOR DETECTING AN ADENOMA-ADENOCARCINOMA TRANSITION IN CANCER

FIELD

The present invention generally relates to colorectal cancer (CRC) and methods of localizing tumor stem cell foci and identifying a colonic tumor having a cancer stem cell (CSC)-like zone and/or having a capacity for marked expansion of tumor cells.

BACKGROUND

The colon has numerous simple and tubular glands and a mixture of mucus secreting goblet cells and water absorbing cells. These glands are called glands because they secrete mucus into the lumen of the colon. When these glands undergo a number of changes at the genetic level, they proceed in a predictable manner as they move from benign to an invasive, malignant colon cancer.

Stepwise acquisition of genetic changes is well known to characterize the development of tumor progression in CRC. The sequence of events that transform an adenoma to an adenocarcinoma begins with multiple mutations in the genes that regulate cell division and apoptosis. Over a series of cell divisions the mutations become increasingly prevalent among the cells, resulting in dysplasia and ultimately cancer. These mutational events are correlated with discrete morphologic transitions from hyperplastic to adenomatous areas followed by in situ transformation and finally invasive carcinoma. The genetic drivers for each stage of this process, however, have not been fully established.

Colon tissue contains layers of specific compartments called crypts, which contain several different types of cells including stem cells. Low numbers of stem cells are present at the base of these crypts. Normally, these stem cells produce new, proliferating cells, which become differentiating cells as they travel up the crypt and replace older apoptotic cells (dying cells). Regulated growth of the epithelium in the normal colon is driven by these crypt-localized intestinal stem cells (ISC) that alternate between quiescent and proliferative states [1]. Shifts in the subcellular localization of the Wnt-associated β-catenin (CTNNB1) complex and signaling through the transforming growth factor (TGF)-β and PTEN/PIK3CA/AKT pathways have been shown to influence ISC cycling [2,3].

By analogy to ISC, a phenotypically and functionally similar population of cancer stem cells (CSC) has been postulated to occur in CRC and other tumors [4,5]. However, tumor progression in CRC is more frequently modeled as stepwise morphologically observable transitions from hyperplastic mucosal changes, to adenomatous areas to in situ malignant transformation and finally invasive carcinoma, as represented by the conceptual Vogelgram [6,7]. Stepwise acquisition of genetic changes also characterize the development of CRC, and in this model, increasing rates of proliferation and genetic instability lead to progressively more dysregulated and growth factor-independent growth.

To date, it remains problematic how the discontinuous model of proliferation and quiescence that underlies the CSC model can be easily reconciled with the incremental evolutionary model represented by the Vogelgram [8]. Furthermore, the genetic drivers for each stage of the Vogelgram process have not been fully established and can be confounded by tumor heterogeneity. Colorectal adenoma vs. adenocarcinoma and carcinoma typically are distinguished by the assessing the presence or absence of multiple morphological characteristics seen in the tumor and surrounding tissue. For example, a colorectal adenoma with benign misplacement of glands usually lacks significant architectural and/or cytologic atypia and exhibits strong collagen type IV continuously around epithelial nests. By contrast, colorectal adenoma containing invasive adenocarcinoma usually exhibits significant architectural and/or cytological atypia and weak, discontinuous collagen type IV. However, methods for distinguishing these types of growths can be multifaceted and challenging.

Accordingly, it would beneficial to identify easily assessed biomarkers of key morphogenetic transitions in colonic tumors such as those present in CRC. The ability to identify signs of emerging invasive CRC additionally would be desirable.

SUMMARY

Provided herein are methods for identifying a cancer stem cell (CSC)-like zone in a colonic tumor, comprising assaying a colonic tumor sample for PTEN expression and detecting an alternating spatial pattern of PTEN expression in the colonic tumor sample. In accordance with the method, the presence of the alternating spatial pattern of PTEN expression is indicative of the presence of a CSC-like region.

Methods for identifying an adenoma-adenocarcinoma (Ad-ACA) transition zone in a colonic tumor and for identifying a colonic tumor that contains high-grade adenoma and early adenocarcinoma regions also are disclosed. These methods comprise assaying a colonic tumor sample for PTEN expression and detecting an alternating spatial pattern of PTEN expression in the colonic tumor sample. The presence of the alternating spatial pattern of PTEN expression indicates high-grade adenoma and early adenocarcinoma regions in the tumor and further identifies the adenoma-adenocarcinoma (Ad-ACA) transition zone in the tumor.

A method for identifying CSCS in a colonic tumor (such as that present in CRC) also is provided, comprising assaying a colonic tumor sample for PTEN expression and detecting an alternating spatial pattern of PTEN expression in the colonic tumor sample. CSCs are identified in the colonic tumor where the alternating spatial pattern of PTEN expression is detected, thus signifying the presence of CSCs. In some embodiments, identified CSCs are further isolated from the tumor tissue (such as from a tumor tissue section using, for example, manual macrodissection or laser capture microdissection).

The present invention further provides a method for diagnosing a subject with high-grade colon adenoma and/or early adenocarcinoma, and a method for determining the likelihood that a colonic tumor in a subject will undergo invasive transformation, if left untreated. These methods comprise assaying a colonic tumor sample for PTEN expression and detecting an alternating spatial pattern of PTEN expression in the colonic tumor sample. The alternating spatial pattern of PTEN expression indicates the presence of high-grade colon adenoma and early adenocarcinoma and it also indicates that the tumor will likely undergo invasive transformation if left untreated.

In some embodiments of the disclosed methods, PTEN expression is assayed by performing immunohistochemistry on a tissue section of the colonic tumor sample with an antibody that specifically binds PTEN, to detect PTEN protein expression.

In some embodiments, the colonic tumor sample is obtained from a subject with CRC and the colonic tumor sample is a colorectal cancer tumor sample.

In some embodiments, the methods provided by the present invention further comprise assaying the colonic tumor for SMAD4 expression, and detecting an alternating spatial pattern of SMAD4 expression in the colonic tumor. The assayed SMAD4 expression may be SMAD4 protein expression and may be assayed by performing immunohistochemistry on a tissue section of the colonic tumor sample with an antibody that specifically binds SMAD4.

In some embodiments, the alternating spatial SMAD4 expression is inversely correlated with the alternating PTEN spatial expression.

In some embodiments, the methods provided by the present invention further comprise assaying a colonic tumor for TP53 expression, and detecting an alternating spatial pattern of TP53 expression in the colonic tumor; and/or assaying the colonic tumor for CD44 expression, and detecting a CD44 expression that is downregulated and redistributed to the basal epithelium border in areas where PTEN protein expression is absent; and/or assaying the colonic tumor for ALDH1 and EZH2 expression, and detecting expression of these markers that is downregulated in parallel with PTEN protein expression.

In some embodiments, the methods of the invention further comprise assaying the colonic tumor for beta-catenin expression and detecting beta-catenin nuclear translocation in tumor cells. The nuclear beta-catenin expression may be correlated with PTEN expression.

In some embodiments, the methods of the invention further comprise assaying the colonic tumor for at least one of Ki-67 expression, MYC expression, MGMT expression, and Rel A/p65 expression, and detecting zonal variations in the further assayed expression(s).

In some embodiments, the genomic DNA of the assayed colonic tumor exhibits at least one of SMAD4 haploinsufficiency and PTEN haploinsufficiency.

The invention further provides a method for identifying a subject with colorectal cancer (CRC) as likely to respond favorably to treatment with a NF-kB pathway targeted therapy, comprising assaying a CRC tumor sample from the subject for PTEN expression and RelA/p65 expression, detecting an alternating spatial pattern of PTEN expression and an alternating spatial pattern of RelA/p65 expression in the tumor sample, and identifying the subject as likely to respond favorably to treatment with a NF-kB pathway targeted therapy when the alternating spatial patterns of PTEN expression and RelA/p65 expression are detected, thereby indicating that the subject will likely respond favorably to treatment with a NF-kB pathway targeted therapy.

A method for determining the likelihood that a subject with CRC will respond favorably to treatment with a TGF-beta pathway targeted therapy also is provided, comprising assaying a CRC tumor sample from the subject for PTEN expression and SMAD4 expression, detecting an alternating spatial pattern of PTEN expression and an alternating spatial pattern of SMAD4 expression in the tumor sample, and identifying the subject as likely to respond favorably to treatment with a TGF-beta pathway targeted therapy when the alternating spatial patterns of PTEN expression and SMAD4 expression in the tumor sample are detected, thereby indicating that the subject will likely respond favorably to treatment with a TGF-beta pathway targeted therapy.

Another aspect of the invention provides a method for identifying an individual with 18q/SMAD4 genomic loss, comprising assaying a colonic tumor sample from an individual for SMAD4 expression, detecting an alternating spatial pattern of SMAD4 expression in the tumor sample, and determining the individual has 18q/SMAD4 genomic loss when the alternating spatial SMAD4 expression is detected. In this aspect, the alternating SMAD4 spatial expression indicates that the genomic DNA of the tumor likely has 18q/SMAD4 genomic loss.

Another aspect of the invention provides a method for identifying an individual with 10q/PTEN genomic loss, comprising assaying a colonic tumor sample from an individual, detecting the presence of alternating spatial pattern of PTEN expression in the tumor sample, and determining the individual has 10q/PTEN genomic loss when the alternating spatial PTEN expression is detected. In this aspect, the alternating PTEN spatial expression indicates that the genomic DNA of the tumor likely has 10q/PTEN genomic loss.

In some embodiments, assaying a colonic tumor sample for expression comprises assaying the tumor sample for protein expression. Assaying protein expression may comprise performing immunohistochemistry on a tissue section of the colonic tumor sample with an antibody that specifically binds to the assayed protein(s).

Another aspect of the invention provides kits comprising at least one reagent that detects PTEN expression in a tissue sample. In some embodiments, a kit further comprises a reagent that detects the expression of at least one protein or nucleic acid selected from the group consisting of SMAD4, TP53, ALDH1 and CD44. In one embodiment, the reagents are antibodies that specifically bind to the recited proteins and the kit is a basic kit that comprises an antibody that specifically binds to PTEN, an antibody that specifically binds to SMAD4, an antibody that specifically binds to TP53 and an antibody that specifically binds to CD44.

In some embodiments, a kit further comprises at least one antibody selected from the group consisting of an antibody that specifically binds to beta catenin, an antibody that specifically binds to EZH2, an antibody that specifically binds to MYC and an antibody that specifically binds to RelA/p65.

DETAILED DESCRIPTION

Definitions

Figure 1:
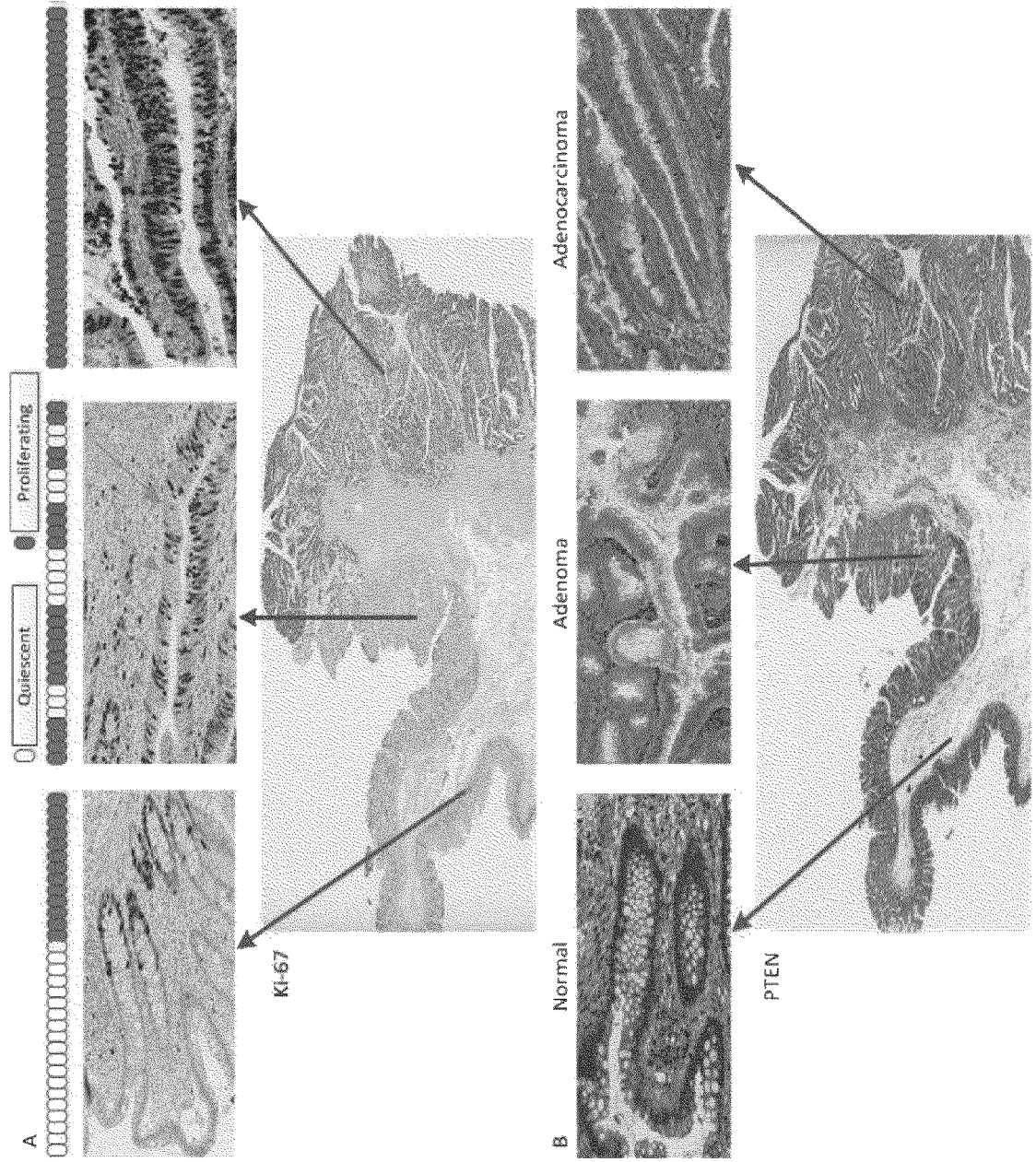
FIG. 1. An alternating pattern of Ki-67 and PTEN at the adenoma (Ad)-adenocarcinoma (ACA) transition. (A/Top panels) Ki-67 immunohistochemical staining of a primary colon cancer section shows proliferating cells restricted to the crypts in normal/hyperplastic epithelium (left), stretches of alternating Ki-67+ proliferating and Ki-67-quiescent cells in the adenomatous region adjacent to the first areas of invasive tumor (middle) and uniform proliferation in the majority of the invasive carcinoma (right). (B/Bottom panels) PTEN immunostaining from the same tumor showing uniform PTEN expression in the normal/hyperplastic epithelium (left), most of the adenomatous epithelium and in the invasive tumor (right). An area within the Ad-ACA transitional zone shows on-off alternating PTEN expression (middle).

As used herein, the phrases "alternating expression," "alternating spatial expression" or "alternating spatial pattern of expression" refer to a spatial pattern of multifocal zonal loss and gain (also described as the spatially alternating presence and absence) of protein expression or nucleic acid expression. Such alternating expression may be intraglandular. In this regard, "alternating PTEN expression" refers to the spatially alternating PTEN protein presence and absence or alternating PTEN nucleic acid presence and absence as seen in a tissue section slide (i.e., and "on/off" repeating pattern of staining).

"Alternating SMAD4 expression" that is "inversely related" to PTEN expression refers to alternating SMAD4 protein or nucleic acid expression in a tissue wherein the areas of SMAD4 staining or presence in the tissue correspond to areas of PTEN absence and areas of SMAD4 absence in a tissue correspond to areas of PTEN staining or presence.

"Haploinsufficiency" as used herein means only a single functional copy of a gene is present in a cell, tissue, or organism, with the other copy of the gene inactivated by mutation.

"Adenoma" as used herein refers to a benign tumor of the epithelium arising from or resembling a gland and usually grows into the lumen of an organ. An adenoma may be pedunculated (lobular head with a long slender stalk) or sessile (broad base). An adenomatous polyp is an exemplary type of colonic adenoma. Adenomatous proliferation is characterized by different degrees of cell dysplasia (atypia or loss of normal differentiation of epithelium) irregular cells with hyperchromatic nuclei, (pseudo)stratified nuclei, nucleolus, decreased mucosecretion, and mitosis. The architecture may be tubular, villous, or tubulo-villous. Basement membrane and muscularis mucosae are intact.

"Adenocarcinoma" is neoplasia of epithelial tissue that has glandular origin, glandular characteristics, or both and is the malignant counterpart to adenoma. In some embodiments of the invention, an adenocarcinoma is an adenocarcinoma not otherwise specified (adenocarcinoma NOS). In some embodiments, a colonic adenocarcinoma appears grossly as a mass that looks of a different color than the surrounding tissue and the tumor cells have a large nucleus with prominent nucleoli. Adenocarcinoma tumor cells may exhibit a noticeable increase in the incidence of mitosis.

The "adenoma-adenocarcinoma junction" (also referred to as the adenoma-adenocarcinoma transition) as recited herein refers to a region of adenomatous epithelium adjacent to invasive carcinoma in a colonic tumor.

A "colonic tumor" as used herein refers to an abnormal mass of tissue in the colon that is the result of abnormal growth or division of cells and includes benign, pre-malignant and malignant tumors located in the colon. A CRC tumor is one type of colonic tumor. The growth of the tumor cells exceeds, and is not coordinated with, that of the normal tissues around it. In some embodiments a colonic tumor comprises colonic epithelial cells.

A "cancer stem cell (CSC)-like zone" or "cancer stem cell (CSC)-like adenoma-adenocarcinoma (Ad-ACA) transition" as used herein refers to a region of the Ad-ACA junction that exhibits high genetic stability and high genomic complexity preceding the emergence of a more uniform, invasive CRC clone. This zone further exhibits zonal variations in CSC markers such as beta-catenin and/or MGMT and may exhibit basally-redistributed CD44. The presence of this zone, thus, indicates the presence of a forerunner colonic lesion that is associated with malignant transformation and the presence of adenomatous-carcinoma transition.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., Molec. Immunol. 26:403-11 (1989). The antibodies can be recombinant monoclonal antibodies produced according to the methods disclosed in U.S. Pat. No. 4,474,893 or 4,816,567. The antibodies can also be chemically constructed according to the method disclosed in U.S. Pat. No. 4,676,980. The antibody can further be a single chain antibody or bispecific antibody.

An "antibody" includes antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) Science 254:1275-1281).

Monoclonal antibodies can be produced in a hybridoma cell line according to the technique of Kohler and Milstein, (1975) Nature 265:495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as E. coli by recombinant techniques known to those skilled in the art. See, e.g., W. Huse, (1989) Science 246:1275-81.

Antibodies can also be obtained by phage display techniques known in the art or by immunizing a heterologous host with a cell containing an epitope of interest.

The terms "specific binding" or "specifically binds" as used herein, in reference to the interaction of an antibody, a protein, or a peptide with a second chemical species, mean that the interaction is dependent upon the presence of a particular structure (e.g., an antigenic determinant or epitope) on the chemical species. An antibody that "specifically binds to" or is "specific for" a particular polypeptide or an epitope on a particular polypeptide is one that binds to that particular polypeptide or epitope on a particular polypeptide preferentially (i.e., without substantially binding to any other polypeptide or polypeptide epitope). For example, an antibody recognizes and specifically binds to a specific protein structure rather than to all proteins generally. If an antibody is specific for epitope "A", the presence of a molecule containing epitope A (or free, unlabeled A), in a reaction containing labeled "A" and the antibody, will reduce the amount of labeled A bound to the antibody.

"In situ hybridization" (ISH) as used herein refers to a type of hybridization process that uses a labeled oligonucleotide probe (a complementary DNA or RNA strand) to localize a specific "target" DNA or RNA sequence in a portion or section of tissue (in situ) by hybridizing to that target sequence. The probe may be labeled directly or indirectly either before hybridizing to the target sequence or after hybridization. The label is a detectable label.

An "oligo-SNP genomic array" is a type of DNA microarray that is used to detect polymorphisms within a population such as single nucleotide polymorphisms (SNPs), which are variation at a single site in DNA. An oligo-SNP genomic array includes an array containing immobilized nucleic acid target sequences, one or more labeled oligonucleotide probes and a detection system that records and interprets a hybridization signal. One exemplary oligo-SNP array is the Genomic Alterations, Postnatal, ClariSure® Oligo-SNP Array (Quest Diagnostics, Madison, N.J.).

"Isolated" cells such as isolated CSCs are cells that have been removed from their natural presence in a tissue or organism. CSCs that are isolated from a tissue slide or section have been separated from that slide or section. Although isolated cells may be purified, "isolated" does not require that a cell is pure of any other cell types or tissue components.

A tissue sample is "limited" when the amount of the sample obtained or biopsied is not abundant.

"PTEN" refers to phosphatase and tensin homolog. The PTEN gene is located from base pair 89,623,194 to base pair 89,728,531 on chromosome 10. An exemplary PTEN amino acid sequence is that of NCBI/Genbank accession no. AAH05821.

"SMAD4" refers to SMAD family member 4. The SMAD4 gene is located from base pair 48,556,582 to base pair 48,611,411 on chromosome 18. An exemplary SMAD4 amino acid sequence is that of NCBI/Genbank accession no. BAB40977.

"TP53" refers to tumor protein p53 (also known as tumor suppressor p53). The TP53 gene is located from base pair 7,571,719 to base pair 7,590,867 on chromosome 17. An exemplary TP53 amino acid sequence is that of NCBI/Genbank accession no. AEX20383.

"CD44" refers to CD44 molecule. The CD44 gene is located from base pair 35,160,416 to base pair 35,253,948 on chromosome 11 and encodes a CD44 cell-surface glycoprotein. An exemplary CD44 amino acid sequence is that of NCBI/Genbank accession no. ACI46596.

"Ki-67" refers to cell proliferation antigen Ki-67. An exemplary amino acid sequence for Ki-67 is Genbank accession no. B48666.

"MYC" (also known as c-Myc) refers to v-myc avian myelocytomatosis viral oncogene homolog. The MYC gene is located from base pair 128,748,314 to base pair 128,753,679 on chromosome 8 and encodes multifunctional, nuclear phosphoprotein. An exemplary MYC amino acid sequence is that of NCBI/Genbank accession no. AAA59887.

"MGMT" refers to O-6-methylguanine-DNA methyltransferase. An exemplary MGMT amino acid sequence is that of NCBI/Genbank accession no. NP_002403.

"Rel A/p65" refers to v-rel avian reticuloendotheliosis viral oncogene homolog A (also known as p65 or NF-kB p65 subunit). It is encoded by the REL gene located from base pair 61,108,708 to base pair 61,171,409 on chromosome 2.

"AKT" refers to v-akt murine thymoma viral oncogene homolog 1 (also known as AKT1 or PKB). The AKT gene is located from base pair 105,235,685 to base pair 105,262,079 on chromosome 14 and the encoded AKT protein is a protein kinase.

"TCL1" refers to T-cell leukemia/lymphoma protein 1A.

"EZH2" refers to enhancer of zeste homolog 2. It encodes an EZH2 enzyme, which forms part of a protein group called the polycomb repressive complex-2. The EZH2 gene is located from base pair 148,504,463 to base pair 148,581,440 on chromosome 7. An exemplary EZH2 amino acid sequence is that of NCBI/Genbank accession no. AAS09975.

"Beta-catenin" refers to cadherin-associated protein, beta 1, 88 kDa. It is encoded by the CTNNB1 gene, which is located from base pair 41,236,400 to base pair 41,281,938 on chromosome 3.

"Cyclin-D1" is also known as CCND1 (gene). The CCND1 gene encodes a cyclin-D1 protein, which belongs to the highly conserved cyclin family, whose members are characterized by a dramatic periodicity in protein abundance throughout the cell cycle. The CCND1 gene is located from base pair 69,455,872 to base pair 69,469,241 on chromosome 11.

"ALDH1" refers to aldehyde dehydrogenase 1 family.

DESCRIPTION

Described herein are methods for identifying colonic tumors that exhibit a clearly distinct zone of rapidly spatially alternating proliferative and hypoproliferative/quiescent colonic epithelium where numerous intestinal stem cell (ISC)/cancer stem cell (CSC) markers are also modulated in parallel. This CSC-like transition zone occurs in the pre-invasive adenomatous epithelium immediately adjacent to invasive areas of a tumor (i.e., the adenoma-adenocarcinoma (Ad-ACA) junction). This is in contrast with the more uniform proliferation and more homogenous expression profiles of the deeper, invasive adenocarcinoma (ACA) and the adenomatous areas adjacent to non-neoplastic epithelium.

Determining whether a colonic tumor is an adenoma as opposed to a adenocarcinoma or an invasive carcinoma can be important for deciding the appropriate subsequent course of action and/or treatment to employ (i.e., simple polyp removal as opposed to more aggressive methods such as, for example, chemotherapy).

This CSC-like zone is present in a significant percentage of CRC cases with morphologically-intact Ad-ACA junctions. Accordingly, disclosed herein are methods for their detection.

Not to be bound by theory, it is believed that this zone in other CRC cases is obliterated by overgrowth of the invasive component or is not sampled (and, therefore, not seen) due to incomplete sectioning of the tumor, or is difficult to visualize due to the complex architecture of some tumors. Additionally, for any given marker, aberrant absence or overexpression due to genetic mutation or gene deletion can mask the transition zone. This happens frequently with SMAD4 where mutation or loss of heterozygosity (LOH) can result in uniform complete loss of expression of that protein. Therefore, disclosed herein is a panel of markers for detecting the Ad-ACA transition zone with the highest sensitivity.

In some cases, this transition zone shows haploinsufficiency of PTEN through genomic deletion and modulation of the TGF-beta pathway as detected by SMAD expression. This transitional zone, which may be overgrown by the invasive component in some tumors, appears to represent activation of an intestinal stem cell (ISC)-like phenotype only during a particular temperospatial stage in the development of CRC.

Methods of Detection

Accordingly, provided herein are methods for identifying a CSC-like region in a colonic tumor, identifying a adenoma-adenocarcinoma (Ad-ACA) transition zone in a CRC tumor, identifying a colonic tumor that contains high-grade adenoma and/or early adenocarcinoma regions, identifying CSC in a colonic tumor such as a CRC tumor, diagnosing a subject with high-grade colon adenoma and/or early adenocarcinoma, and determining the likelihood that a colon tumor in a subject will undergo invasive transformation if left untreated, the methods comprising assaying a colonic for PTEN expression and detecting an alternating spatial pattern of PTEN expression in the tumor sample.

In some embodiments, the methods comprise assaying a colonic or CRC tumor sample for PTEN protein expression, and detecting an alternating spatial pattern of PTEN protein expression in the tumor sample. The alternating spatial pattern of expression establishes the location of a CSC-like zone at the Ad-ACA junction in the tumor tissue.

Spatially alternating PTEN expression may correlate with similar alternating spatial expression of cancer stem/progenitor cell markers such as, for example, beta-catenin/CTNNB1, ALDH1 and/or CD44. Furthermore, in some instances with preserved morphologic transitions, the alternating PTEN expression is observed in a zone of adenomatous epithelium located immediately adjacent to the invasive tumor component and is correlated with intraglandular stretches of alternating Ki-67 expression in addition to expression of other cell cycle mediators and growth regulators such as SMAD4. Accordingly, in some embodiments, the disclosed methods further comprise assaying expression of at least one, two, three, four or all of these proteins and, optionally, detecting alternating spatial expression of at least one, two, three, four or all of them.

The present inventors have identified a distinctive CSC-like pre-invasive transitional stage of PTEN-haploinsufficient CRC that is followed by the emergence of one or several invasive tumor clones with dysregulated TP53 and a more stable proliferation pattern and expression profile. Accordingly, some embodiments of the invention further comprise assaying at least one of SMAD4, and TP53 and detecting their alternating spatial expression in the tumor sample. In some embodiments, protein expression of one or more of ALDH1, EZH2, Ki-67, MYC and RelA/p65 also are assayed and found to exhibit alternating spatial expression in the tumor sample. CD44 also may be assayed and CD44 protein expression that is downregulated and redistributed to the basal epithelium border in areas where PTEN protein expression is absent may be detected.

In some embodiments, one or more of the above specified protein markers (such as, for example, PTEN and SMAD4), are assayed to complement a morphologic examination when identifying an Ad-ACA morphogenetic transition, especially in situations of limited tissue samples.

Another aspect of the invention provides a method of identifying an individual with 10q/PTEN genomic loss, comprising assaying a colorectal cancer tumor sample from an individual, detecting an alternating spatial pattern of PTEN protein expression in the tumor sample, and determining the individual has 10q/PTEN genomic loss when the alternating spatial PTEN protein expression is detected.

Another aspect of the invention provides a method of identifying an individual with 18q/SMAD4 genomic loss, comprising assaying a colonic or a colorectal cancer tumor sample from an individual, detecting an alternating spatial pattern of SMAD4 protein expression in the tumor sample, and determining the individual has 18q/SMAD4 genomic loss when the alternating spatial SMAD4 protein expression is detected.

A further aspect of the invention provides methods for identifying a subject with CRC as likely to respond favorably to treatment with a TGF-beta targeted therapy or NF-kB pathway targeted therapy by assaying PTEN and SMAD4 or PTEN and p65/RelA, respectively, in a colonic tumor sample or a CRC tumor sample and detecting their alternating spatial expressions. "Responding favorably" to treatment means that at least one detectable sign of the CRC is reduced at least partially after treatment.

Samples

The disclosed methods may be performed on a colonic tissue sample such as, for example, a colonic tumor sample, a colonic polyp, a CRC tumor biopsy or another sample of the innermost lining of the colon (the mucosa). Preferably, one or more sections of a tissue samples is/are assayed. In some embodiments, serial sections of a tumor are assayed.

In some embodiments, a tumor sample is obtained from a subject suspected of having colon cancer, a subject in need of a diagnosis regarding colon cancer or in need of colon tumor staging, and/or a subject undergoing a colonoscopy. A subject may have tested positive for colonic polyps and/or may have colorectal cancer.

In a specific embodiment, a colonic biopsy is obtained from a human subject and analyzed according to the methods of the invention. Upon detecting the PTEN and/or other protein alternating spatial expression as disclosed herein, it may be determined that further biopsies or exploratory procedures (such as, for example, surgery) are needed for an accurate diagnosis or to remove the base of an incompletely resected polyp or other colonic lesions.

Assaying Methods

In some embodiments, the assaying performed in the methods disclosed herein comprises detecting a protein (such as, for example, PTEN) on a tissue section by immunostaining. In some embodiments, the assaying comprises performing immunohistochemistry (IHC) on the tissue section with an antibody that specifically binds a protein of interest (such as, for example, PTEN). The antibody may be detectably labeled or it may bind to a detectably labeled compound. Proteins that may be assayed to determine the presence or absence of their alternating spatial expression include one or more proteins selected from the group consisting of ALDH1, b-catenin, CD44, EZH2, c-Myc, cyclin-D1, EZH2, MGMT, p53, PTEN, p-SMAD1/5/8, and SMAD4.

Immunohistochemistry protocols are well known in the art. Other methods may be used to detect specific immunological binding of an antibody to a protein either directly or indirectly. Hereunder, the antibody-to-protein pair shall be understood to include either a primary antibody directed to the protein to be analyzed (e.g. PTEN or SMAD4) or a secondary antibody directed to the primary antibody. Preferred examples of suitable detection methods according to the present invention are luminescence, particularly fluorescence, furthermore VIS coloring and/or radioactive emission.

Luminescence concerns the emission of light as a result of chemiluminescence, bioluminescence or photoluminescence. Chemiluminescence involves the emission of visible light as a result of a chemical reaction, whereas bioluminescence requires the activity of luciferase. The presently preferred photoluminescence, which is also known as fluorescence stimulation, is caused by the absorption of photons, preferably provided by radiation, which is released again as photon with a shift in wavelength of 30 to 50 nm and within a period of approximately $10^{-8}$ seconds. The instruments for fluorescence detection include, but are not limited to typical bench top fluorometers, fluorescence multi-well plate readers, fiber optic fluorometers, fluorescence microscopes and microchips/microfluidics systems coupled with fluorescence detection.

VIS coloring denotes the visualization of any achromatic substance in order to be visible to the naked eye. Preferably, the intensity of coloring is measured by a photometer.

Radioactive radiation of isotopes is measured by scintillation. The process of liquid scintillation involves the detection of beta decay within a sample via capture of beta emissions in a system of organic solvents and solutes referred to as the scintillation cocktail. The beta decay electron emitted by radioactive isotopes such as $^3$H, $^{14}$C, $^{32}$P, $^{33}$P and $^{35}$S in the sample excites the solvent molecule, which in turn transfers the energy to the solute. The energy emission of the solute (the light photon) is converted into an electrical signal by a photo-multiplier tube within a scintillation counter. The cocktail must also act as a solubilizing agent keeping a uniform suspension of the sample. Gamma ray photons often arise as a result of other decay processes (series decay) to rid the newly formed nucleus of excess energy. They have no mass and produce little if any direct ionization by collision along their path. Gamma photons are absorbed for detection and quantization by one or more of three mechanisms: the Compton Effect, the photoelectric effect and pair production. A favorable gamma decay isotope of the present invention is $^{125}$I.

Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine.

Indirect labels include various enzymes well known in the art, such as horseradish peroxidase (HRP), alkaline phosphatase (AP), β-galactosidase, urease and the like. The covalent linkage of an anti-integrin antibody to an enzyme may be performed by different methods, such as the coupling with glutaraldehyde. Both, the enzyme and the antibody are Interlinked with glutaraldehyde via free amino groups, and the by-products of networked enzymes and antibodies are removed. In another method, the enzyme is coupled to the antibody via sugar residues if it is a glycoprotein, such as peroxidase. The enzyme is oxidized by sodium periodate and directly interlinked with amino groups of the antibody. Other enzyme containing carbohydrates can also be coupled to the antibody in this manner. Enzyme coupling may also be performed by interlinking the amino groups of the antibody with free thiol groups of an enzyme, such as .beta.-galactosidase, using a heterobifunctional linker, such as succinimidyl 6-(N-maleimido) hexanoate. The horseradish-peroxidase detection system can be used, for example, with the chromogenic substrate tetramethylbenzidine (TMB), which yields a soluble product in the presence of hydrogen peroxide that is detectable at 450 nm. The alkaline phosphatase detection system can be used with the chromogenic substrate p-nitrophenyl phosphate, for example, which yields a soluble product readily detectable at 405 nm. Similarly, the β-galactosidase detection system can be used with the chromogenic substrate o-nitrophenyl-β-D-galactopyranoxide (ONPG), which yields a soluble product detectable at 410 nm. A urease detection system can be used with a substrate, such as urea-bromocresol purple.

Antibodies used to detect a protein in a tissue section may be labeled with detectable moieties, which include, but are not limited to, radionuclides, fluorescent dyes, e.g. fluorescein, fluorescein isothiocyanate (FITC), Oregon Green™, rhodamine, Texas red, tetrarhodimine isothiocynate (TRITC), Cy3, Cy5, etc., fluorescent markers, e.g. green fluorescent protein (GFP), phycoerythrin, etc., autoquenched fluorescent compounds that are activated by tumor-associated proteases, enzymes, e.g. luciferase, HRP, AP, etc., nanoparticles, biotin, digoxigenin, and the like.

One or more protein markers may be used alone or in combination (including as double IHC, triple IHC, etc.) in the assaying step of the methods provided herein.

In some embodiments, analysis of a marker expression is done by fluorescent in-situ hybridization (FISH) or oligo-SNP genomic arrays.

Other methods of detecting marker protein or nucleic acid expression on tissue sections are well known in the art and may be employed to assess alternating spatial expression of the disclosed markers in colonic tissue.

Kits

The invention further provides kits for identifying an adenoma-adenocarcinoma transition region and/or a CSC-like zone in a colonic tissue sample (such as a CRC tumor), comprising one or more reagents that detect marker proteins of interest.

As used herein, a "kit" refers to a packaged collection of components such as, for example, isolated oligonucleotide primers, probes, and/or isolated antibodies and additional associated reagents. Non-limiting examples of materials in which kit components may be packaged include boxes, bags, envelopes and tubes, but kit components may be supplied to a consumer in additional types of packages. In some embodiments, isolated antibodies and/or other reagents included in a kit are supplied in tubes, vials or other types of containers within the kit.

In some embodiments a kit further contains instructions for using the kit components. The instructions may be printed on a material within the kit or on the kit packaging or supplied in electronic format. In some embodiments, the instructions specify how to detect expression such as, for example, spatially alternating protein expression in a tissue sample using the specific components (e.g., primers, probe(s), antibodies, and/or other reagents) contained in the kit.

In some embodiments, the kit contains one or more reagents that detect a PTEN protein, and one or more reagents that detect a SMAD4 protein.

In some embodiments, a kit further comprises one or more reagents that detect TP53, and/or one or more reagents that detect CD44.

In further embodiments, an expanded kit may additionally comprise one or more reagents that detect at least one marker selected from the group consisting of a beta catenin, ALDH1, EZH2, MYC and RelA/p65.

In some embodiments, the reagents specifically detect a specified marker protein. In some embodiments, the reagents specifically detect a nucleic acid encoding a specified marker protein. In some embodiments, a reagent that specifically detects a specified protein comprises an antibody that specifically binds to that protein. Some kits comprise a secondary antibody that detects a primary antibody. In some embodiments an antibody in the kit comprises a detectable label or binds either directly or indirectly to a compound that is or comprises a detectable label.

EXAMPLES

Example 1—Downmodulation, Deletion and Re-Expression of PTEN During Genomic Progression of Colorectal Cancer Background/Methods:

A common genetic change in CRC is silencing of the AKT regulator PTEN. However, variations in PTEN levels occur that indicate more complex stage-specific regulation. CRC was studied using immunohistochemistry (IHC) on FFPE sections of primary adenocarcinoma (ACA) for PTEN (6H2.1) and TP53 (BP53-11), and FISH was performed for PTEN using the CL PTEN/GRID1 probe. An oligo-SNP microarray (OSA) was performed on FFPE-extracted DNA using CytoScan HD 2.6 arrays.

TABLE 1

PTEN Findings in Colorectal Cancer.

| | | PTEN IHC Pattern (n = 726) | | | FISH in PTEN dim or negative cases (n = 37) | | |
|---|---|---|---|---|---|---|---|
| | Intact | Uniformly Decreased | Complete Loss | Heterogeneous (off-on pattern) | No loss | PTEN- | PTEN-/- |
| Frequency | 320 (44.1%) | 317 (43.8%) | 39 (7.2%) | 50 (6.8%) | 13 (35%) | 17 (46%) | 7 (19%) |
| Pattern of loss | — | AD/early ACA, reexpressed or lost in deep ACA | ACA with no AD | AD/early ACA, reexpressed in deeper ACA | 70% of loss/het IHC cases have PTEN deletion vs. 25% of intact/decreased cases (p = 0.014) | | |

Results:

There were 4 PTEN expression patterns in primary CRC (Table 1). Most common were intact PTEN expression and uniformly decreased expression (compared to non-neoplastic epithelium) in adenomatous areas (AD) with progressively dimmer expression in the ACA. Cases with complete PTEN loss were uncommon and restricted to ACAs with minimal/absent AD. A distinctive heterogeneous (het) group showed PTEN variation restricted to the AD-ACA junction with PTEN reexpression in the ACA.

PTEN genomic deletion by FISH was more common in the loss and het groups and rare in the intact or downregulated cases.

By OSA, het PTEN cases were mostly genetically complex with PTEN genomic deletion (12/18, 67%) associated with 18q21/SMAD4 (11/18, 61%) and 17p13/TP53 loss (8/18, 44%). OSA performed on macrodissected het samples demonstrated a reversal of PTEN genomic loss when PTEN protein was reexpressed in the ACA areas in 4/5 (80%); TP53 expression was also dysregulated.

Conclusions:

In the vast majority of primary CRC, PTEN modulation is either not observed or shows downregulation at the adenoma stage without genomic deletion. In this group, PTEN levels usually decline with the adenoma-carcinoma transition suggesting gradual epigenetic silencing. Abrupt loss of PTEN expression is uncommon, associated with PTEN deletion and in tumors that lack an Ad-ACA transition. In the distinctive PTEN-het cases, levels fluctuate only at the Ad-ACA transition and reexpression occurs with tumor progression, often associated with TP53 dysregulation.

Example 2—A Transition Zone Showing Highly Discontinuous or Rapidly Alternating Levels of Stem Cell and Proliferation Markers Characterizes the Development of Colorectal Cancer Background:

Stepwise acquisition of genetic changes characterizes the development of CRC. These mutational events are correlated with discrete morphologic transitions from hyperplastic to adenomatous areas followed by in situ transformation and finally invasive carcinoma. The goal of this study was to identify easily assessed biomarkers of key morphogenetic transitions in CRC.

Methods:

Case Selection and Immunohistochemistry:

Cases include primary CRC cases submitted for molecular or immunophenotyping to Quest Diagnostics Nichols Institute. Material used was excess/discarded formalin-fixed paraffin-embedded (FFPE) tissue sections with samples anonymized prior to study inclusion with no identifying patient information retained. Cases included were a random selection of primary colon tumors with adequate FFPE tissue sections. The location or absence in each case of morphologic transitions from normal to hyperplastic mucosa, hyperplastic to adenomatous changes (Ad), and adenomatous change to in situ and invasive adenocarcinoma (ACA) were recorded.

Immunohistochemistry was performed on 4 micron FFPE sections using the Bond Max III (Leica Microsystems, Wetzlar, Germany), Ultra Benchmark (Ventana, Tucson, Ariz.) and Link (Dako, Carpinteria, Calif.) automated staining platforms, with epitope retrieval performed on-instrument for Leica (Epitope Retrieval Solution 2, pH 9.0 buffer) and Ventana (Cell Conditioner 1, pH 9.0 buffer) and offline for the Dako platform (TRS, pH 9.0 buffer for 40 minutes). The list of antibody clones and working dilutions are listed in Table 2. A peroxidase block was applied to all slides prior to antibody application. Primary antibodies incubations were at room temperature for 12-32 minutes, with detection using 3,3-Diaminobenzidine (DAB) (DAB, including Bond Polymer Refine for Leica, UltraView DAB for Ventana and Envision for Dako). Slides were counterstained with hematoxylin and post-counterstained with bluing.

TABLE 2

Antibodies utilized for immunohistochemistry

| Antibody | Antibody Documentation | | |
|---|---|---|---|
| | Clone | Dilution | Supplier |
| ALDH1a1 | EP1933Y | 1:300 | Biocare Medical; Concord, CA |
| Beta-Catenin | β-Catenin-1 | undiluted | Dako North America, Inc; Carpenteria, CA |
| CD44 | MRQ-L3 | undiluted | Cell Marque; Rocklin, CA |
| c-Myc | EP121/Y69 | 1:150 | Epitomics, Inc.; Burlingame, CA |
| cyclin-D1 | SP4 | undiluted | Ventana Medical Systems; Tuscon, AZ |
| EZH2 | D2C9 | 1:100 | Cell Signaling Technology; Danvers MA |
| MGMT | MT3.1 | 1:175 | Millipore; Bellerica; MA |
| P53 | Bp53-11 | undiluted | Ventana Medical Systems: Tuscon, AZ |
| PTEN | 6H2 | 1:100 | Dako North America, Inc.; Carpenteria, CA |
| p-SMAD1/5/8 | Ser463/465 | 1:250 | Santa Cruz Biotech; Santa Cruz, CA |
| SMAD4 | B-8 | 1:300 | Santa Cruz Biotech; Santa Cruz, CA |

Immunostains were scored semi-quantitatively by two of the authors (KA, DJ), with images captured using the Aperio XT slide scanner to assess subcellular stain localization. For Ki-67, the pattern and number of cells with strong nuclear positivity were recorded; PTEN staining was scored as: uniform/normal in tumor, down regulated in tumor compared to adjacent normal colon, complete/zonal loss of staining in all or part of the tumors and as having a multifocal oscillating pattern with areas of loss juxtaposed next to tumor cells with a normal pattern (Table 3). For other markers, including ALDH1, β-Catenin, CD44, cyclin D1, EZH2, MGMT P53, p-SMAD (1/5/8) and SMAD4, staining was assessed with regards to level across tumor in relation to non-neoplastic epithelium and/or admixed lymphocytes as well as the subcellular localization (nuclear, cytoplasmic, membrane or combinations).

TABLE 3

Patterns of PTEN immunohistochemistry expression in primary CRC

| | PTEN IHC Expression Pattern | | | |
|---|---|---|---|---|
| | Normal | Down Regulated | Complete/ Zonal Loss | Alternating Pattern |
| All CRC cases tested (n = 735) | 277/735 (37.7%) | 275/735 (37.4%) | 89/735 (12.1%) | 94/735 (12.8%) |
| Only CRC cases with intact Ad-ACA transition (n = 202) | 66/202 (32.7%) | 57/202 (28.2%) | 4/202 (2.0%)*' | 75/202 (37.1%)* |

*'p < 0.0001, lower in cases with preserved Ad-ACA (Fisher's exact)
*p < 0.0001, higher in cases with preserved Ad-ACA (Fisher's exact)

Fluorescent In Situ Hybridization:

Glass slides containing 4-μm FFPE sections were baked at 56° C. overnight then dewaxed and rehydrated using xylene and ethanol. Slides were treated using 0.2 N HCl, formalin, a pretreatment wash, and protease prior to adding the FISH probe. Samples were then co-denatured at 72° C. for 5 minutes and allowed hybridized overnight (14-18 hours) in a humidity chamber set to 37° C. Slides were probed using Metasystems CL PTEN/GRID1, 3-color deletion probe (MetaSystems, D-5971-100-TC). The PTEN locus specific probe is labeled in orange at a 315 kb region on chromosome band 10q23.3. Additional probes in the cocktail included a locus-specific probe for GRID1 located at chromosome band 10q23.2, labeled in green, and a probe for the centromeric control region (10p11.1-q11.1) labeled in blue.

To establish a normal cutoff value for scoring, 100 tumor cells were counted for 10 cases with normal colon epithelium were counted. Slides were categorized as a heterozygous deletion if more than 10% of cells had a single copy loss, a homozygous deletion if more than 10% of cells had a biallelic loss, and normal if less than 10% of cells had a deletion. Slides were evaluated by comparing the number of PTEN signals to each of the two control regions on the PTEN/GRID1 probe (i.e., 2R2G2B for normal, R2G2B for single loss, and 2G2B for biallelic loss). Slides were scored using the above criteria, in conjunction with a marked IHC slide to identify regions with loss of PTEN expression.

Oligonucleotide/SNP Array (OSA):

Genomic DNA was extracted using QiaAmp DNA FFPE Tissue Kit (Qiagen, Valencia, Calif.), following macrodissection of FFPE tumor sections, and assessed using the CytoScan HD 2.6 million-probe microarray platform (Affymetrix, Santa Clara, Calif.) following manufacturer's instructions. Up to 1 μg DNA was digested with the restriction enzyme Nsp I, ligated to adaptors, and amplified with PCR. The product was then purified using a magnetic separation technique, fragmented, and labeled before hybridization to the microarray. Sample quality was assessed at the PCR purification step. Samples with prominent CSC-like Ad-ACA transition regions were macrodissected and analyzed independently from the more deeply invasive ACA, in 5 cases.

Results were analyzed using Chromosome Analysis Suite (ChAS) software (Affymetrix). For comparisons of frequency of IHC patterns and abnormal loci by OSA in CSC-like cases with cases with intact PTEN, p-values were generated using Fisher's exact test.

Mutation Analysis:

Mutational analysis on genomic DNA extracted from macrodissected tumor in FFPE sections was performed for the exon 3 hotspot of CTNNB1 and exons 11 and 15 of BRAF by PCR-based DNA Sanger sequencing, with an approximate sensitivity of 10-15% mutated alleles, and for PIK3CA (hotspots in exons 9 and 20) and KRAS (codons 12, 13 and 61) by pyrosequencing, with an approximate 2-5% sensitivity. In 11 cases with prominent CSC-like transition zones, sequencing was performed for mutation hotspots in 34 cancer-associated genes, which additionally included PTEN, SMAD4 and TP53, using the Ampliseq Cancer array (Life Technologies, Carlsbad, Calif.). Protocol was per manufacturer's instructions with DNA sequencing performed on the Ion PGM platform and data analyzed using SequencePilot software (JSI MedSystems, Germany).

Results:

A Highly Discontinuous Pattern of Proliferation and of PTEN and SMAD4 Expression Characterizes the Adenoma-Adenocarcinoma Transition in a Subset of Colorectal Tumors The pattern of expression of a variety of proliferation markers across the morphologic transitions in well-oriented FFPE tumor sections of primary CRC was examined. In a subset of CRC, a localized zone was identified that showed striking intraglandular alteration between Ki-67+ proliferative and Ki-67-hypoproliferative stretches of adenomatous epithelium (Ad) in an area adjacent to invasive carcinoma (ACA). These zones of discontinuous Ki-67 expression often occurred over a stretch of 10 to several hundred tumor cells (FIG. 1). Despite the striking alternating IHC pattern, Ki-67+ and Ki-67 stretches were largely morphologically indistinguishable from each other and were not present in the normal/hyperplastic epithelial transition or in the invasive carcinoma. In a subset of cases examined, a parallel discontinuous expression of multiple cell cycle regulators including cyclin D1, MYC and P53 also was noted in these Ad-ACA transition zones (FIG. 2 and not shown).

The growth regulator PTEN also demonstrated similar and overlapping abrupt intragland alterations in protein levels with highly discrete/discontinuous on-off borders (FIG. 1B). These occurred in the same areas at the Ad-ACA junction where PTEN expression correlated with Ki-67 positivity (FIG. 2). This on/off Ad-ACA transitional zone, as detected by PTEN IHC, was prominent in 50/735 (6.8%) of all CRC cases studied but was at least focally present in 75/202 (37.1%) cases with intact Ad-ACA junctions (Table 3).

This alternating pattern was distinct from the downregulated but still uniformly expressed PTEN IHC pattern seen in the majority of CRC and the complete PTEN loss pattern seen in a smaller subset of ACA (Table 3). Furthermore, even in cases with prominent alternating PTEN at the Ad-ACA transition, the invasive ACA always showed reexpression of PTEN in the invasive areas. This pattern of alternating PTEN expression was not observed in 20 conventional colonic adenomas without associated invasive carcinoma (not shown). Nearly all CRC cases with abrupt and irreversible loss of PTEN expression by IHC did not have identifiable Ad-ACA junctions (85/89; 95.5%) and also lacked a preceding alternating on/off pattern of PTEN expression.

Figure 2:
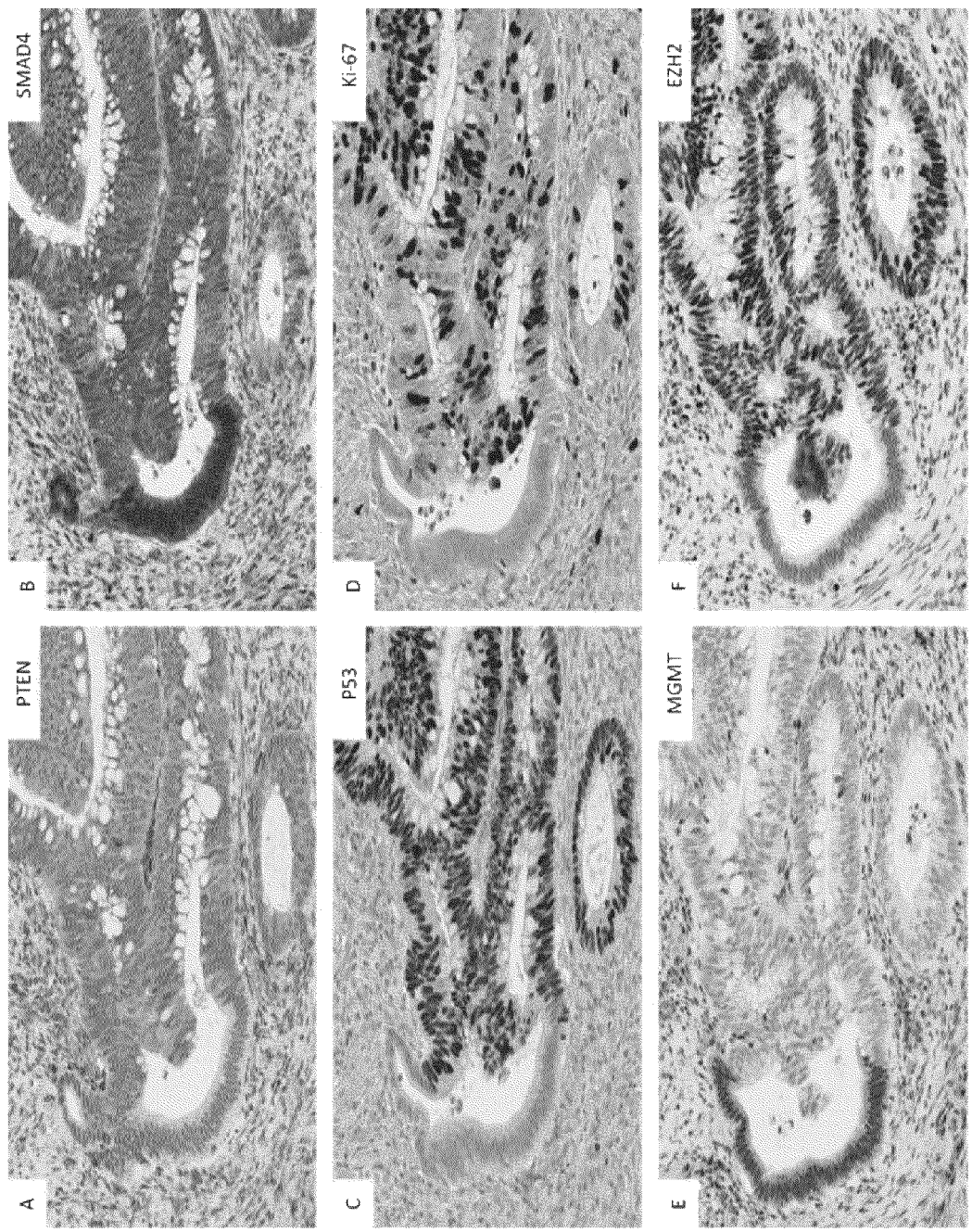
FIG. 2. Synchronous modulation of proliferation and cancer stem cell marker expression focally in the Ad-ACA transitional zone. Immunostaining in the Ad-ACA transition zones of another primary CRC tumor showing focal loss of PTEN, Ki-67, P53 and EZH2 in the same portion of the gland that shows upregulation of SMAD4 and MGMT.

In a smaller subset of cases examined, SMAD4, a mediator of TGF-beta signaling, also showed on-off protein modulation in these same areas (FIG. 2). Serial section staining and PTEN-SMAD4 double immunostaining (not shown) showed a largely inverse relationship between the SMAD+ and PTEN+ cells. Dynamic alterations in TGF-beta pathway signaling was also suggested by the nuclear/cytoplasmic shifts in phospho-SMAD1/5/8 IHC staining in these areas (not shown).

Figure 3:
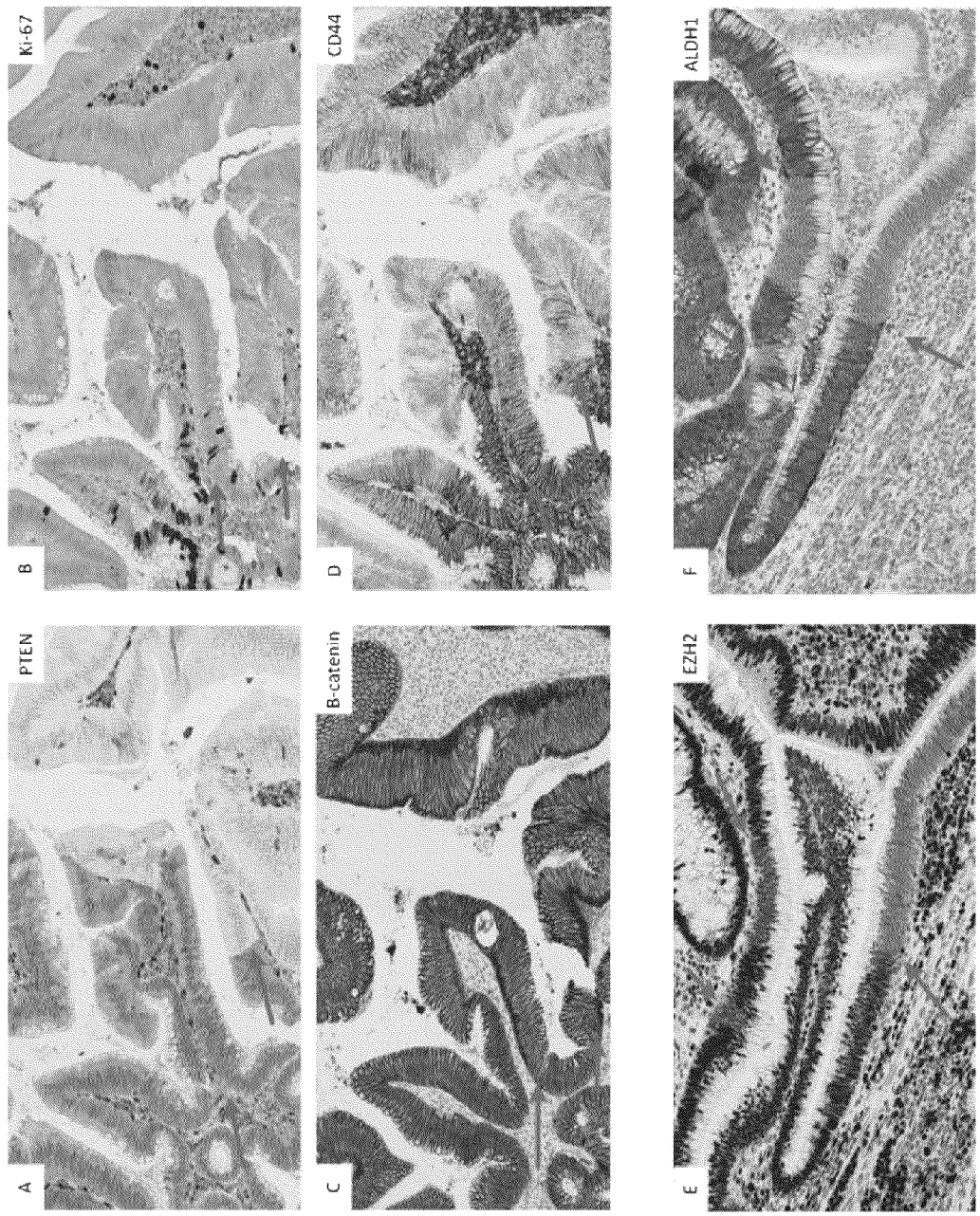
FIG. 3. Multifocal alternating proliferation and cancer stem cell marker expression in a tumor with a prominent CSC-like Ad-ACA transitional zone (A-D) Adenomatous epithelium adjacent to with prominent multifocal zones of PTEN loss and decreased Ki-67, with nuclear-localization of beta-catenin and decreased levels and basal membrane relocalization of CD44. (E,F) The Ad-ACA transition in another tumor shows multifocal stretches of adenomatous epithelium with loss of EZH2 and ALDH1 expression.

Multiple Cancer Stem Cell Markers and the Beta-Catenin/EZH2 Complex Show Rapid Alteration Along with PTEN at the Ad-ACA Transition Given the role of PTEN/AKT signaling in mediating ISC cycling, the level and subcellular localization of CSC markers [4,9] in these transitional areas was examined. PTEN-alternating proliferative/hypoproliferative zones also showed dramatic discontinuity in the expression of stem cell markers ALDH1, EZH2 and MGMT, the levels and localization of CD44, and shifts in cytoplasmic/membrane and nuclear localization of beta-catenin (FIGS. 2 and 3). In the stretches of cells with low-to-absent PTEN and Ki-67 positivity, beta-catenin was shifted to the nucleus (FIG. 3A-C).

Away from the Ad-ACA transition zones, beta-catenin was either fully translocated to the nucleus or present in membrane/cytoplasmic locations in nearly all cells with only scattered single cells or small clusters of cells with nuclear-localized protein. CD44 was both downregulated and redistributed to the basal epithelium border in PTEN-areas (FIG. 3D). MGMT was upregulated in areas that showed downregulation/absence of EZH2 and ALDH1 staining.

The exact phase of the alternating marker expression was variable at Ad-ACA transitions in some tumors. In general, the Ki-67+ proliferative zones showed a PTEN+ P53+ EZH2low ADLH1-MGMThigh SMAD4-immunophenotype with inverse phenotype in the Ki-67-quiescent zones, as shown in FIG. 2. However, precise overlap in the on/off boundary for each marker in the Ad-ACA transition region was unusual. More typically, as shown in FIG. 3, were zonal correlations indicating slightly different phases of downregulation or upregulation for some markers.

Figure 4:
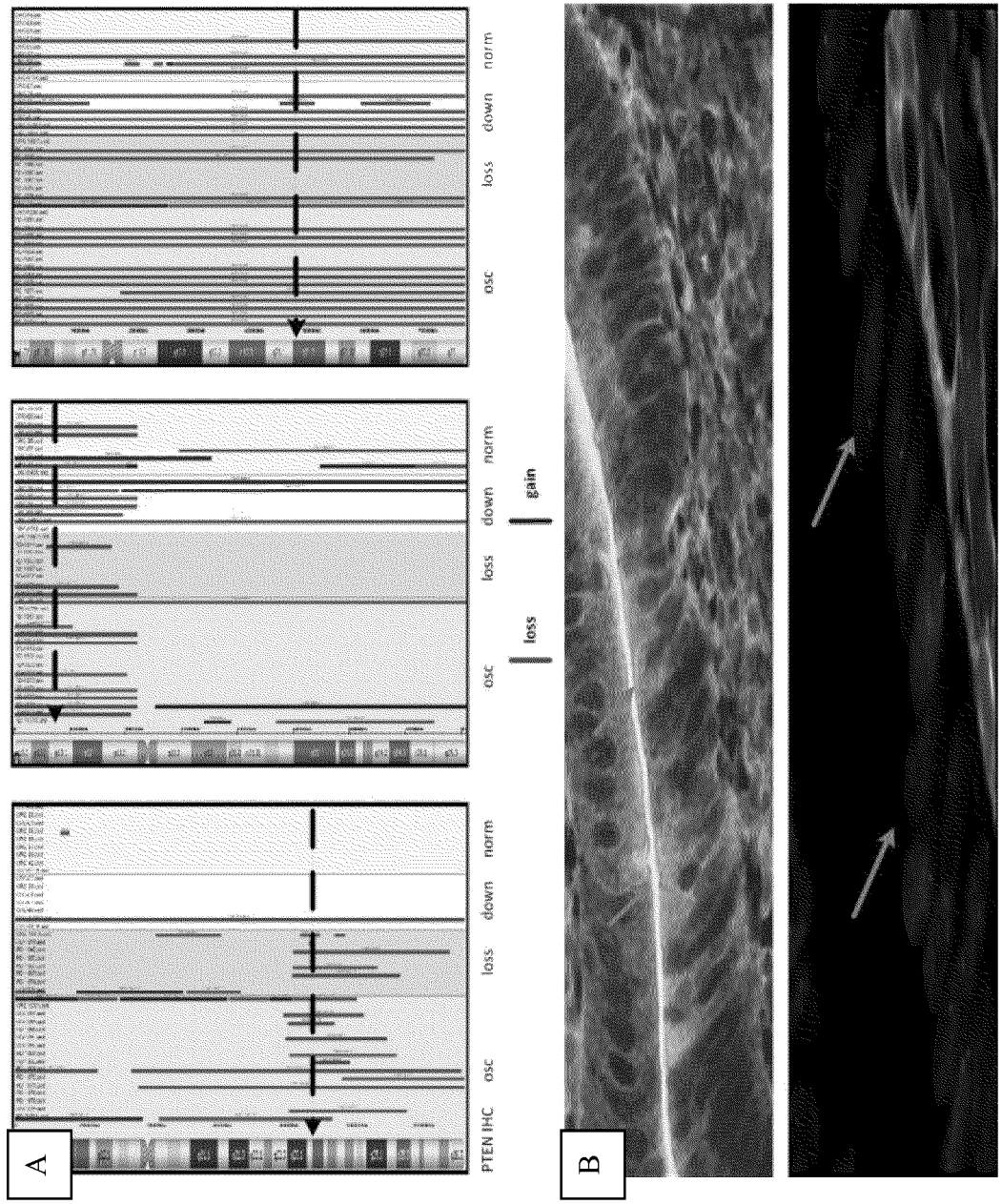
FIG. 4. PTEN deletion is highly associated with tumor with a prominent CSC-like transition zone. (A) Oligonucleotide/SNP array results show frequent deletion (red lines) of the PTEN locus on chromosome 10 (black dotted arrow) in CRC with prominent CSC-like transitions/alternating PTEN (blue background) and complete PTEN loss by IHC (pink background) as compared to those with uniform PTEN downmodulation or normal expression (white and yellow background). Cases with deletions of the p arm of chromosome 17 encompassing TP53 (middle) and deletions of chromosome 18 (right) were commonly noted in CRC regardless of PTEN IHC pattern. (B) High magnification of PTEN IHC (above) in a CSC-like transition with the matched PTEN FISH image of a serial section (below) shows a heterogeneous pattern of chromosome 10 copy number in the epithelial cells consistent with predominantly haploinsufficient PTEN loss.

CRC with Prominent CSC-Like Transition Zones were Highly Associated with Haploinsufficiency for PTEN In CRC cases with prominent CSC-like transition zones, the overall genomic findings were examined by OSA (Table 4) and the mutational findings were examined by sequencing panels including for PTEN, SMAD4, TP53 and CTNNB1. CSC-like cases to cases with other patterns of PTEN expression (FIG. 4A). KRAS mutations were present in 83/178 (46.7%) of CSC-like cases, a frequency not significantly different from other PTEN expression subgroups. In a subset of 11 cases with prominent CSC-like transition zones, there was a similar frequency of TP53 (3/11, 27.3%), SMAD4 (2/11, 18.1%), APC and CTNNB1 mutations as expected in unselected CRC cases.

Phenotypic Shifts in P53 Expression in Invasive CRC Away from the CSC-Like Zone; Expression Status at the Ad-ACA Junction and in the Invasive Tumor Compartment With the exception of MGMT, which show more complex variable on/off expression pattern in most tumors, the studied markers that were alternating within the Ad-ACA transition zone were uniformly expressed at other tumor locations. As noted above, cases with prominent alternating PTEN expression at the transition always re-expressed the protein in the invasive tumors; a similar pattern was seen for ALDH1 and EZH2. However, SMAD4 and CD44 expression was occasionally completely lost in the invasive tumor. Most striking, however, was P53 expression, there was a high rate of complete loss (50%) or uniform gain (41.7%) of TP53 expression in the invasive ACA away from the Ad-

TABLE 4

Genomic findings by OSA in primary CRC: comparison of tumors with prominent CSC-like transitions compared to those with intact uniform PTEN expression

| Chromosomal Loci Altered | Altered in Cases with Loss or Prominent CSC-like Transition | Altered in Cases with Uniform PTEN Expression | p-value* | Type of Alteration | Genes in internal related to CRC Pathogensis |
|---|---|---|---|---|---|
| 5q12.2q12.3 | 41.7% (10/24) | 43.8% (7/16) | 1.0 | Loss | |
| 8p23.2p22 | 41.7% (10/24) | 50% (8/16) | 0.74 | Loss | CSMD1, CTSB |
| 10q23.31 | 62.5% (15/24) | 6.3% (1/16) | 0.0007 | Loss | PTEN |
| 13q12.11q34 | 41.7% (10/24) | 62.5% (10/16) | 0.33 | Gain | CDX2, FLT1, PDS5B, STARS13, GAS6 |
| 15q14q15.2 | 41.7% (10/24) | 37.5% (6/16) | 1.0 | Loss | THBS1, BUB1B, RAD51 |
| 15q24.1q25.1 | 45.8% (11/24) | 31.3 (5/16) | 0.51 | Loss | NEIL1 |
| 17p13.2p13.1 | 50% (12/24) | 50% (8/16) | 1.0 | Loss | TP53, AURKB |
| 18p1132p11.31 | 34.2% (13/24) | 62.5% (10/16) | 0.75 | Loss | YES1, EMILIN2 |
| 18q11.2q12.1 | 58.3% (14/24) | 56.3% (9/16) | 1.0 | Loss | |
| 18q12.1q22.3 | 62.5% (15/24) | 62.5% (10/16) | 1.0 | Loss | SMAD2, SMAD4, DCC, SMAD7 |
| 20p11.21p11.1 | 45.8% (11/24) | 50% (8/16) | 1.0 | Gain | |
| 20q11.21q13.33 | 62.5% (15/24) | 62.5% (10/16) | 1.0 | Gain | ID1, BCL2L1, MMP9, AURKA, BMP7 |

*p-values were calculated using the Fisher's exact (two-tailed) test. Using a 2 × 2 contingency table: rows were genomic locus altered or genomic locus normal and columns were PTEN IHC loss/CSC group and PTEN normal or downregulated groups.

In CRC with prominent CSC-like expansion, as defined by the PTEN IHC pattern, the frequency of genomic loss at 10q/PTEN as assessed by OSA (10/16; 62.5%) was much higher than in cases with intact/non-oscillating PTEN expression (6.3% (1/16; 6.3%, p=0.0007) (FIG. 4A). In CSC-like cases, the frequency of PTEN deletion was even higher (13/17; 76.4%) when assayed by FISH. Using FISH, the genetic complement in individual cells within the CSC-like zone was also assessed. In areas with rapid alterations of PTEN and other markers, variation in copy number of several chromosomes by FISH as well as variations in PTEN copy number was noted (FIG. 4B/C).

The high frequency of PTEN deletion in CSC-like tumors was similar in these cases as to those that showed complete PTEN loss by IHC. In the latter group, however, levels of 10q loss by OSA in a subset of cases were consistent with biallelic deletion (not shown). Detectable PTEN mutations were uncommon in all groups.

Figure 5:
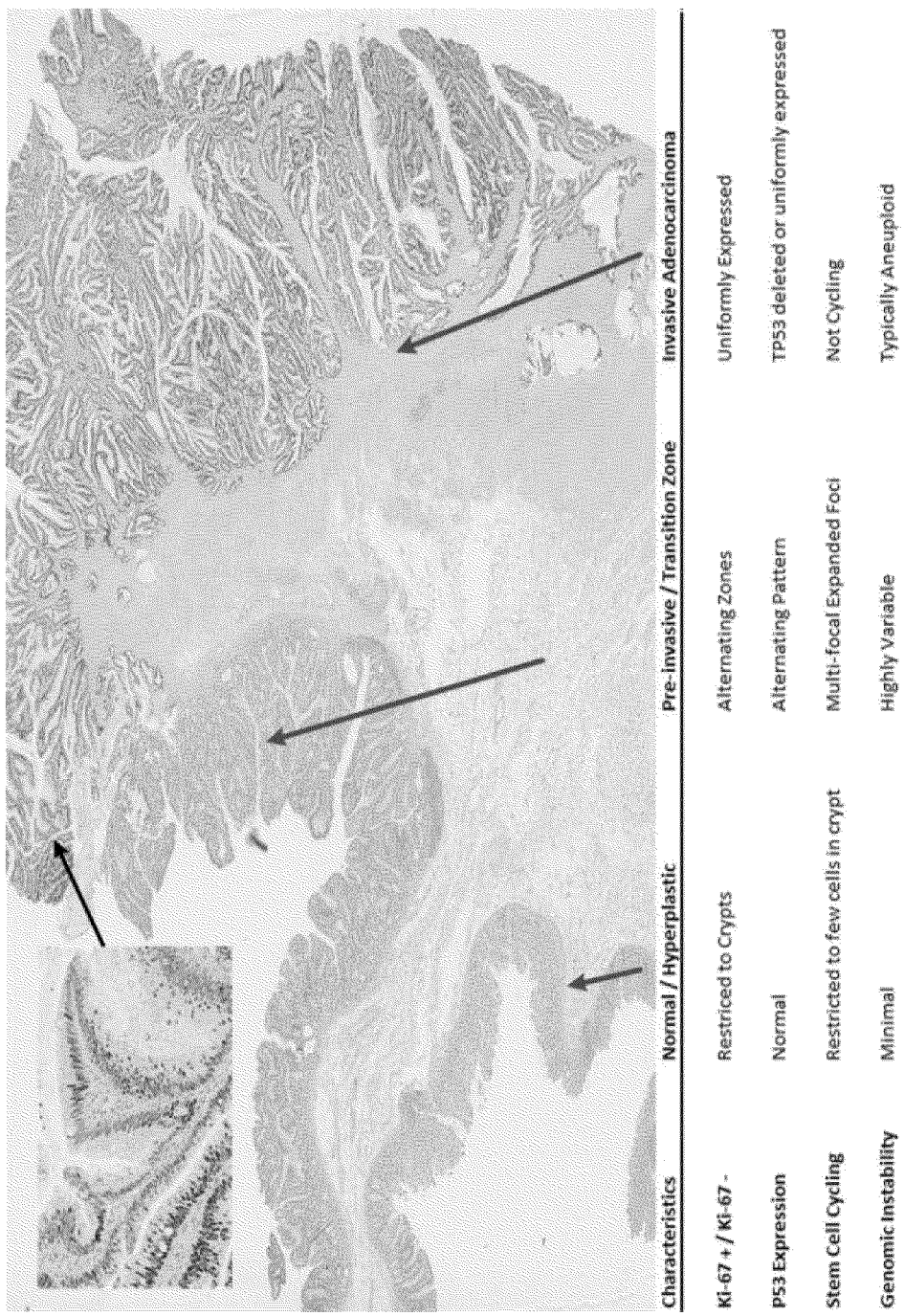
FIG. 5. Uniform TP53 dysregulation in colon carcinoma occurring following the CSC-like transition zone. P53 IHC shows only single cell/focal expression in the normal epithelium and most adenomatous areas, alternating expression in pre-invasive/transition zone (inset) and uniformly upregulated P53 protein expression in the later stages of the invasive adenocarcinoma. This case is the same as the one illustrated in FIG. 1. The common features of each morphologic transition in CRC cases with prominent CSC-like features are shown below.

The frequency of genetic alterations at chr 18q/SMAD4 12/16 (75%) and chr 17p/TP53 9/16 (56.3%) was similar in ACA transition (FIG. 5). In these tumors, the alternating P53 expression seen within the CSC-like transition zones was no longer observed.

The pattern of proliferation and expression of growth regulatory and stem cell markers across distinct morphologic transition zones in 726 cases of CRC was examined. In cases with preserved adenoma-carcinoma morphologic transitions, a characteristic zone of adenomatous epithelium, often located immediately adjacent to and extending into the invasive component, that showed rapidly oscillating intraglandular stretches of Ki-67+ and Ki-67− cells was identified. This pattern correlated with oscillating expression of other cell cycle mediators and the growth regulators PTEN and SMAD4. These multifocal stretches of adenomatous epithelium showed alternating positive/negative expression boundaries. They also demonstrated similar abrupt intragland oscillations in the levels and/or subcellular localization of multiple cancer stem cell (CSC) markers including beta-catenin/CTNNB1, MGMT and CD44.

In contrast, the expression levels of most of these markers were largely homogeneous in the proximal adenomatous and deeper invasive carcinoma surrounding the transitional region. This CSC-like transitional zone, as detected by PTEN IHC, was prominent in 50/726 of all CRC (6.9%) but at least focally present in 97/201 (48.2%) cases with intact adenomacarcinoma junctions. Genomic microarray (ONCOSCAN™ HD) and mutation analysis (AMPLISEQ™) on CRC with prominent CSC-like expansions demonstrated complex genomic changes in 10/16 (62.5%) with a similar frequency of KRAS, BRAF and CTNNB1 mutations as expected in unselected CRC cases. The transition zones in these cases also frequently demonstrated unstable genomes from cell-to-cell (as assessed by FISH) indicating high genetic instability in these areas.

Discussion/Conclusions:

By examination of the morphogenetic transition zones in a large number of primary CRC tumors, a localized CSC-like transition zone of multifocal alternating quiescent/proliferative adenomatous epithelium affecting multiple stem cell and cell cycle markers, including Ki-67, ALDH1, beta-catenin, CD44, EZH2, MGMT, MYC, PTEN, P53 and SMAD4 was uncovered. The CSC-like pre-invasive transition zone in PTEN-haploinsufficient CRC exhibits convergent on-off regulation of the PTEN/AKT, TGF-β/SMAD and Wnt/β-catenin pathways. This bottleneck-like zone is followed by the emergence of invasive tumors with intact PTEN expression but dysregulated TP53 and uniformly high proliferation rates. This transition zone is centered in the pre-invasive adenomatous epithelium adjacent to invasive tumor areas and contrasts with the more uniform proliferation and more homogeneous expression profiles of the deeper invasive ACA and the adenomatous areas adjacent to non-neoplastic epithelium.

Although this CSC-like zone is prominent in only a small percentage of CRC cases as in FIG. 3, it is focally present in a significant percentage of cases with morphologically-intact Ad-ACA transitions, as in FIG. 2. The existence of these discrete CSC-like zones at the Ad-ACA junction in many primary CRCs suggests their detection may serve as a forerunner lesion, predicting incipient invasive transformation. Widely available markers, such as PTEN and SMAD4, could be used alone or in combination (including as double IHC) to complement morphologic examination in identifying Ad-ACA morphogenetic transition in limited tissue samples.

It is suspected that evidence of this zone in other CRC cases is obliterated by overgrowth of the invasive component or is not sampled due to incomplete sectioning of the tumor, or is difficult to visualize due to the complex architecture of some tumors. Additionally, for any given marker, aberrant absence or overexpression due to genetic mutation or gene deletion can mask the transition zone. This happens frequently with SMAD4 where mutation or LOH can result in uniform complete loss of expression of that protein. Therefore, a panel of markers is needed to detect the Ad-ACA transition zone with the highest sensitivity.

The colocalization but not perfect overlap of the on/off boundaries for many markers suggests that the modulation of the proliferation/quiescent transition is likely quite rapid in these areas. These dyssynchronous boundaries seen in some cases are likely due to varying half-lives and different downregulation mechanisms for each protein, including proteolytic cleavage, transcriptional downregulation and proteosome clearance [10,11]. Nonetheless, Ki-67+/PTEN+/MYC+/TP53+ zones alternating with Ki-67−/MGMT+/beta-cateninnuc/SMAD+ zones is the characteristic pattern seen in many cases.

The highly significant association of PTEN deletion/haploinsufficiency with CRC cases that have prominent CSC-like zones implicates lower levels of the PTEN protein and consequently differential modulation of AKT kinase activity as one trigger for the CSC phenotype. Numerous studies in cell lines and mouse genetic models have supported a role for haploinsufficiency or reduced levels of PTEN in promoting cancer progression [12-14]. Furthermore, cycling of AKT activity, due to PTEN variations or other factors, such as TCL1 oscillation, is also a common finding in both cancer-related and non-neoplastic stem cell function and embryogenesis [15-18]. However, the return of PTEN to normal levels without zonal alterations in the invasive component of these CSC-like tumors implicates coordinate dysregulation of other pathways at the Ad-ACA junction.

In this regard, the absence of detectable Ad/ACA junctions and the absence of a CSC-like alternating phenotype in CRC with total PTEN IHC loss indicates that the natural history of colon tumors with complete PTEN inactivation is distinctive [19].

Given the pattern of alternating markers observed in the transition zones, activating and inhibitory interactions between the TGF-beta/SMAD, PI3K/Akt, and Wnt/beta-catenin signaling pathways are favored [20]. Interactions between AKT and BMP/TGF-beta signaling, as noted here for PTEN and SMAD4, is a feature of the stem cell phenotype in some models [21-23]. The modulation of SMAD signaling (as assessed by phospho-SMAD antibodies) and SMAD4 expression in opposition to PTEN in a number of the CSC-like cases may reflect hyperresponsiveness of the junctional epithelium to BMP/TGF-beta signaling. To help drive the cyclical proliferative/quiescent properties of the transition zone, effects of SMAD activation on inhibition of Wnt signaling [24,25] could oppose the effects of increased EZH2 on driving beta-catenin activity [26].

Another possible coregulator of the CSC-like phenotype at the Ad-ACA transition is MYC which also alternates in parallel with PTEN, Ki-67 and SMAD4. In cell line models, MYC overexpression can drive PTEN upregulation and EZH2 downmodulation through the inhibition of AKT [27]. Once PTEN levels and AKT activity began to oscillate, effects of the broader stem cell transcriptional program are likely [28]. AKT activity in the absence of PTEN has also been shown to promote genetic instability, which is observed at the CSC-like transitions and would tend to promote genetic progression [29].

It is noted that in most CRC with prominent CSC-like zones, TP53 dysregulation, as evidenced by uniform P53 IHC loss or gain, occurs in the invasive tumor away from the transition zone. This suggests that TP53-driven outgrowth of a dominant invasive CRC clone usually follows and is perhaps driven by genetic selection within the CSC-like transition zone. It is possible that these transition zones are a general phenomenon of the pre-invasive stage of carcinogenesis where AKT and Wnt/Beta-catenin are cyclically regulated. The fluctuating TP53 levels and highly regulated proliferative-quiescent transition suggests the zone may function as a tumor bottleneck stage preceding the emergence of more uniformly TP53-dysregulated invasive subclones.

Using a large series of primary CRC tumors, it is shown that in well-oriented tissue sections, colon tumors show a clearly distinct zone of rapidly alternating proliferative and hypoproliferative colonic epithelium where numerous ISC/CSC markers are also modulated in parallel. This transition zone often begins in pre-invasive adenomatous epithelium adjacent to invasive tumor areas that have more uniform proliferation and more homogeneous genetic and expression profiles. This easily assessed phenomenon appears to represent a commonly occurring genetically unstable forerunner or transitional stage in CRC evolution. In addition, this zone, which occurs in the adenomatous transition immediately adjacent to invasive areas of the tumor, shows haploinsufficiency of PTEN through genomic deletion and modulation of the TGF-beta pathway as detected by SMAD expression. This transitional zone, which is likely overgrown by the invasive component in some tumors, appears to represent activation of an ISC-like phenotype only during a particular temperospatial stage in the development of CRC.

Multiple immunohistochemical markers, including PTEN, SMAD4, CD44 and CTNNB1, highlight this localized CSC-like transition zone.

OTHER EMBODIMENTS

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

REFERENCE LIST

1. Clevers H (2013) Stem Cells: A unifying theory for the crypt. Nature 495: 53-54. nature11958 [pii]; 10.1038/nature11958 [doi].
2. Pinto D, Clevers H (2005) Wnt control of stem cells and differentiation in the intestinal epithelium. Exp Cell Res 306: 357-363. S0014-4827(05)00087-X [pii]; 10.1016/j.yexcr.2005.02.022 [doi].
3. Xia D, Srinivas H, Ahn Y H, Sethi G, Sheng X, Yung W K, Xia Q, Chiao P J, Kim H, Brown P H, Wistuba I I, Aggarwal B B, Kurie J M (2007) Mitogen-activated protein kinase kinase-4 promotes cell survival by decreasing PTEN expression through an NF kappa B-dependent pathway. J Biol Chem 282: 3507-3519. M610141200 [pii]; 10.1074/jbc.M610141200 [doi].
4. Hill R, Wu H (2009) PTEN, stem cells, and cancer stem cells. J Biol Chem 284: 11755-11759. R800071200 [pii]; 10.1074/jbc.R800071200 [doi].
5. Du L, Wang H, He L, Zhang J, Ni B, Wang X, Jin H, Cahuzac N, Mehrpour M, Lu Y, Chen Q (2008) CD44 is of functional importance for colorectal cancer stem cells. Clin Cancer Res 14: 6751-6760. 14/21/6751 [pii]; 10.1158/1078-0432.CCR-08-1034 [doi].
6. Cho K R, Vogelstein B (1992) Suppressor gene alterations in the colorectal adenoma-carcinoma sequence. J Cell Biochem Suppl 16G: 137-141.
7. Goldberg D M, Diamandis E P (1993) Models of neoplasia and their diagnostic implications: a historical perspective. Clin Chem 39: 2360-2374.
8. Hammoud S S, Cairns B R, Jones D A (2013) Epigenetic regulation of colon cancer and intestinal stem cells. Curr Opin Cell Biol 25: 177-183. S0955-0674(13)00008-2 [pii]; 10.1016/j.ceb.2013.01.007 [doi].
9. Lugli A, Iezzi G, Hostettler I, Muraro M G, Mele V, Tornillo L, Carafa V, Spagnoli G, Terracciano L, Zlobec I (2010) Prognostic impact of the expression of putative cancer stem cell markers CD133, CD166, CD44s, EpCAM, and ALDH1 in colorectal cancer. Br J Cancer 103: 382-390. 6605762 [pii]; 10.1038/sj.bjc.6605762 [doi].
10. Voutsadakis I A (2008) The ubiquitin-proteasome system in colorectal cancer. Biochim Biophys Acta 1782: 800-808. S0925-4439(08)00130-0 [pii]; 10.1016/j.bbadis.2008.06.007 [doi].
11. Wan M, Cao X, Wu Y, Bai S, Wu L, Shi X, Wang N, Cao X (2002) Jab1 antagonizes TGF-beta signaling by inducing Smad4 degradation. EMBO Rep 3: 171-176. 10.1093/embo-reports/kvf024 [doi]; kvf024 [pii].
12. Trotman L C, Niki M, Dotan Z A, Koutcher J A, Di C A, Xiao A, Khoo A S, Roy-Burman P, Greenberg N M, Van D T, Cordon-Cardo C, Pandolfi P P (2003) Pten dose dictates cancer progression in the prostate. PLoS Biol 1: E59. 10.1371/journal.pbio.0000059 [doi].
13. Hill R, Calvopina J H, Kim C, Wang Y, Dawson D W, Donahue T R, Dry S, Wu H (2010) PTEN loss accelerates KrasG12D-induced pancreatic cancer development. Cancer Res 70: 7114-7124. 0008-5472.CAN-10-1649 [pii]; 10.1158/0008-5472.CAN-10-1649 [doi].
14. Byun D S, Ahmed N, Nasser S, Shin J, Al-Obaidi S, Goel S, Corner G A, Wilson A J, Flanagan D J, Williams D S, Augenlicht L H, Vincan E, Mariadason J M (2011) Intestinal epithelial-specific PTEN inactivation results in tumor formation. Am J Physiol Gastrointest Liver Physiol 301: G856-G864. ajpgi.00178.2011 [pii]; 10.1152/ajpgi.00178.2011 [doi].
15. Narducci M G, Fiorenza M T, Kang S M, Bevilacqua A, Di G M, Remotti D, Picchio M C, Fidanza V, Cooper M D, Croce C M, Mangia F, Russo G (2002) TCL1 participates in early embryonic development and is overexpressed in human seminomas. Proc Natl Acad Sci USA 99: 11712-11717. 10.1073/pnas.182412399 [doi]; 182412399 [pii].
16. Finkielsztein A, Kelly G M (2009) Altering PI3K-Akt signalling in zebrafish embryos affects PTEN phosphorylation and gastrulation. Biol Cell 101: 661-78, 4. BC20090034 [pii]; 10.1042/BC20090034 [doi].
17. Kharas M G, Okabe R, Ganis J J, Gozo M, Khandan T, Paktinat M, Gilliland D G, Gritsman K (2010) Constitutively active AKT depletes hematopoietic stem cells and induces leukemia in mice. Blood 115: 1406-1415. blood-2009-06-229443 [pii]; 10.1182/blood-2009-06-229443 [doi].
18. Lin Y, Yang Y, Li W, Chen Q, Li J, Pan X, Zhou L, Liu C, Chen C, He J, Cao H, Yao H, Zheng L, Xu X, Xia Z, Ren J, Xiao L, Li L, Shen B, Zhou H, Wang Y J (2012) Reciprocal regulation of Akt and Oct4 promotes the self-renewal and survival of embryonal carcinoma cells. Mol Cell 48: 627-640. S1097-2765(12)00774-5 [pii]; 10.1016/j.molcel.2012.08.030 [doi].
19. Naguib A, Cooke J C, Happerfield L, Kerr L, Gay L J, Luben R N, Ball R Y, Mitrou P N, McTaggart A, Arends M J (2011) Alterations in PTEN and PIK3C A in colorectal cancers in the EPIC Norfolk study: associations with clinicopathological and dietary factors. BMC Cancer 11: 123. 1471-2407-11-123 [pii]; 10.1186/1471-2407-11-123 [doi].
20. Lee M Y, Lim H W, Lee S H, Han H J (2009) Smad, PI3K/Akt, and Wnt-dependent signaling pathways are involved in BMP-4-induced ESC self-renewal. Stem Cells 27: 1858-1868. 10.1002/stem.124 [doi].
21. Kobielak K, Stokes N, de la Cruz J, Polak L, Fuchs E (2007) Loss of a quiescent niche but not follicle stem cells in the absence of bone morphogenetic protein signaling. Proc Natl Acad Sci USA 104: 10063-10068. 0703004104 [pii]; 10.1073/pnas.0703004104 [doi].
22. Tian X, Du H, Fu X, Li K, Li A, Zhang Y (2009) Smad4 restoration leads to a suppression of Wnt/beta-catenin signaling activity and migration capacity in human colon carcinoma cells. Biochem Biophys Res Commun 380: 478-483. 50006-291X(09)00133-8 [pii]; 10.1016/j.bbrc.2009.01.124 [doi].
23. Jung C J, Iyengar S, Blahnik K R, Jiang J X, Tahimic C, Torok N J, de vere White R W, Farnham P J, Zern M (2012) Human ESC self-renewal promoting microRNAs induce epithelial-mesenchymal transition in hepatocytes by controlling the PTEN and TGFbeta tumor suppressor signaling pathways. Mol Cancer Res 10: 979-991. 1541-7786.MCR-11-0421 [pii]; 10.1158/1541-7786.MCR-11-0421 [doi].
24. He X C, Zhang J, Tong W G, Tawfik O, Ross J, Scoville D H, Tian Q, Zeng X, He X, Wiedemann L M, Mishina Y, Li L (2004) BMP signaling inhibits intestinal stem cell self-renewal through suppression of Wnt-beta-catenin signaling. Nat Genet 36: 1117-1121. 10.1038/ng1430 [doi]; ng1430 [pii].
25. Freeman T J, Smith J J, Chen X, Washington M K, Roland J T, Means A L, Eschrich S A, Yeatman T J, Deane N G, Beauchamp R D (2012) Smad4-mediated signaling inhibits intestinal neoplasia by inhibiting expression of beta-catenin. Gastroenterology 142: 562-571. 50016-5085(11)01622-2 [pii]; 10.1053/j.gastro.2011.11.026 [doi].
26. Jung H Y, Jun S, Lee M, Kim H C, Wang X, Ji H, McCrea P D, Park J I (2013) PAF and EZH2 Induce Wnt/beta-Catenin Signaling Hyperactivation. Mol Cell 52: 193-205. S1097-2765(13)00628-X [pii]; 10.1016/j.molcel.2013.08.028 [doi].
27. Kaur M, Cole M D (2013) MYC acts via the PTEN tumor suppressor to elicit autoregulation and genome-wide gene repression by activation of the Ezh2 methyltransferase. Cancer Res 73: 695-705. 0008-5472.CAN-12-2522 [pii]; 10.1158/0008-5472.CAN-12-2522 [doi].
28. Ning Z Q, Li J, Arceci R J (2001) Signal transducer and activator of transcription 3 activation is required for Asp(816) mutant c-Kit-mediated cytokine-independent survival and proliferation in human leukemia cells. Blood 97: 3559-3567.
29. Mukherjee A, Karmakar P (2013) Attenuation of PTEN perturbs genomic stability via activation of Akt and down-regulation of Rad51 in human embryonic kidney cells. Mol Carcinog 52: 611-618. 10.1002/mc.21903 [doi].

What is claimed is:

1. A method for isolating a cancer stem cell (CSC) in a colonic tumor, comprising
   a. contacting one or more tissue sections of a colonic tumor sample with an antibody that specifically binds to PTEN and an antibody that specifically binds to SMAD4,
   b. detecting the presence or absence of an alternating spatial pattern of PTEN expression and an alternating spatial pattern of SMAD4 expression, and
   c. identifying the presence of CSCs in the colonic tumor where the alternating spatial pattern of PTEN expression and the alternating spatial pattern of SMAD4 expression are detected or identifying the absence of CSCs in the colonic tumor when the alternating spatial pattern of PTEN expression and the alternating spatial pattern of SMAD4 expression are not detected; and
   d. isolating one or more identified CSCs from the tissue section.

2. The method of claim 1, further comprising detecting the zonal variation of expression of at least one additional marker selected from the group consisting of: ALDH1, beta-catenin, CD44, EZH2, Ki-67, MGMT, MYC, RelA/p65, and TP53.

3. The method of claim 2, wherein the zonal variation of expression of the at least one additional marker is an alternating spatial pattern of TP53 expression in the colonic tumor.

4. The method of claim 2, wherein the zonal variation of expression of the at least one additional marker is a CD44 expression that is downregulated and redistributed to the basal epithelium border in areas where PTEN protein expression is absent.

5. The method of claim 2, wherein the zonal variation of expression of the at least one additional marker is beta-catenin nuclear translocation in tumor cells.

6. The method of claim 5, wherein the nuclear beta-catenin expression is correlated with PTEN expression.

7. The method of claim 3, wherein the assayed TP53 expression is protein expression and the assaying comprises performing immunohistochemistry on a tissue section of the colonic tumor sample with an antibody that specifically binds to the assayed protein.

8. The method of claim 1, wherein the alternating spatial pattern of SMAD4 expression is inversely correlated with the alternating spatial pattern of PTEN expression.

9. A method for isolating a CSC from a colonic tumor, comprising a. assaying a colonic tumor sample for spatial patterns of PTEN expression in one or more colonic tumor tissue sections,
b. detecting an alternating spatial pattern of PTEN expression in the one or more colonic tumor tissue sections,
c. identifying a CSC-like region of the one or more tissue sections where the alternating spatial pattern of PTEN expression is detected, and
d. isolating one or more CSCs from the identified CSC-like region.

10. The method of claim 9, further comprising assaying the colonic tumor sample for spatial patterns of SMAD4 expression in the one or more colonic tumor tissue sections and detecting an alternating pattern of SMAD4 expression in the one or more colonic tumor tissue sections, wherein the alternating spatial pattern of SMAD4 expression is inversely correlated with the alternating spatial pattern of PTEN expression.

11. A method for isolating a CSC from a colonic tumor, comprising
   a. assaying a colonic tumor sample for spatial patterns of SMAD4 expression in a colonic tumor tissue section,
   b. detecting an alternating spatial pattern of SMAD4 expression in the colonic tumor tissue section,
   c. identifying a CSC-like region of the tissue section where the alternating spatial pattern of SMAD4 expression is detected, and
   d. isolating one or more CSCs from the identified CSC-like region.

12. A kit for identifying an adenoma-adenocarcinoma transition region in a colonic tumor sample, consisting of: an antibody that specifically binds to PTEN, an antibody that specifically binds to SMAD4, and one or more antibodies from the group consisting of an antibody that specifically binds to TP53, an antibody that specifically binds to CD44, an antibody that specifically binds to beta catenin, an antibody that specifically binds to EZH2, an antibody that specifically binds to MYC, and an antibody that specifically binds to RelA/p65.

13. The kit of claim 12, consisting of: an antibody that specifically binds to PTEN, an antibody that specifically binds to SMAD4, an antibody that specifically binds to TP53, and an antibody that specifically binds to CD44.

14. The kit of claim 12, consisting of: an antibody that specifically binds to PTEN, an antibody that specifically binds to SMAD4, and at least one antibody selected from the group consisting of an antibody that specifically binds to beta catenin, an antibody that specifically binds to EZH2, an antibody that specifically binds to MYC, and an antibody that specifically binds to RelA/p65.

* * * * *